United States Patent [19]

Tedder et al.

[11] Patent Number: 5,766,570

[45] Date of Patent: Jun. 16, 1998

[54] LYMPHOCYTE ACTIVATION ANTIGENS AND ANTIBODIES THERETO

[75] Inventors: Thomas F. Tedder, Durham; Liang-Ji Zhou, Chapel Hill, both of N.C.

[73] Assignee: Dana-Farber Cancer Institute, Inc., Boston, Mass.

[21] Appl. No.: 428,943

[22] Filed: Apr. 24, 1995

Related U.S. Application Data

[63] Continuation of Ser. No. 233,005, Apr. 24, 1994, Pat. No. 5,710,262, which is a continuation-in-part of Ser. No. 870,029, Apr. 17, 1992, Pat. No. 5,316,920.

[51] Int. Cl.$^6$ .................................................. A61K 51/00
[52] U.S. Cl. ................. 424/1.49; 530/387.1; 530/387.3; 530/388.1; 530/388.22; 530/391.3; 435/240.27
[58] Field of Search ................ 530/387.1, 387.3, 530/388.1, 388.22, 391.3; 435/240.27; 424/1.49

[56] References Cited

U.S. PATENT DOCUMENTS 4,451,570  5/1984  Royston ................................. 435/240
5,223,426  6/1993  Skibbens ............................ 435/240.27

OTHER PUBLICATIONS

Kozlow et al *Blood* 81(2) pp. 454–461 (1993).
Roitt et al Immunology Third Edition Moslog Press, St. Louis (1993) p. 4.3.
Rudinger, Peptide Hormones (Parsons Ed.) University Park Press @Baltimore pp. 1–7 (1976).
Zhou et al, J Immunology 149 pp. 735–742 (1992).
Queen et al, PNAS 36 pp. 10029–10033 (1989).
Williams et al., "The Immunoglobulin Superfamily—Domains for Cell Surface Recognition," *Ann. Rev. Immunol.* 6:381–405 (1988).
Littman et al., "The Isolation and Sequence of the Gene Encoding T8: A Molecule Defining Functional Classes of T–Lymphocytes," *Cell* 40:237–246 (1985).
Johnson et al., "Striking similarities between antigen receptor J pieces and sequence in the second chain of the murine CD8 antigen," *Nature* 323:74–76 (1986).
Aruffo et al., "Molecular cloning of two CD7 (T–Cell leukemia antigen) cDNAs by a COS cell expression system," *EMBO J.* 6:3313–3316 (1987).
Williams et al., "Neuronal Cell Thy–1 Glycoprotein: Homology with Immunoglobulin," *Science* 216:696–703 (1982).
Aruffo et al., "Molecular cloning of a CD28 cDNA by a high–efficiency COS cell expression system," *Proc. Natl. Acad. Sci. USA* 84:8573–8577 (1987).
Brunet et al., "A new member of the immunoglobulin superfamily—CTLA–4," *Nature* 328:267–270 (1987).
Lemke et al., "Isolation and Sequence of a cDNA Encoding the Major Structural Protein of Peripheral Myelin," *Cell* 40:501–508 (1985).
Gold et al., "Isolation of cDNA clones encoding the 20K non–glycosylated polypeptide chain of the human T–cell receptor/T3 complex," *Nature* 321:431–434 (1986).

van den Elsen et al., "Isolation of cDNA clones encoding the 20K T3 glycoprotein of human T–cell receptor complex," *Nature* 312:413–418 (1984).
Hermanson et al., "B29: A member of the immunoglobulin gene superfamily exclusively expressd on B–lineage cells," *Proc. Natl. Acad. Sci. USA* 85:6890–6894 (1988).
Sakaguchi et al., "B lymphocyte lineage–restricted expression of mb–1, a gene with CD3–like structural properties," *EMBO J.* 7:3457–3464 (1988).
Turka et al., "CD28 is an inducible T–cell surface antigen that transduces a proliferative signal in $CD3^+$mature thymocytes," *J. Immunol.* 144:1646–1653 (1990).
Harper et al., "CTLA–4 and CD28 activated lymphocyte molecules are closely related in both mouse and human as to sequence, message expression, gene structure, and chromosomal location," *J. Immunol.* 147:1037–1044 (1991).
Linsley et al., "T–cell antigen CD28 mediates adhesion with B cells by interacting with activation antigen B7/BB–1," *Proc. Natl. Sci. USA* 87:5031–5025 (1990).
Freeman et al., "B7, a new member of the Ig superfamily with unique expression on activated and neoplastic B cells," *J. Immunol.* 143:2714–2722 (1989).
Linsley et al., "CTLA–4 is a second receptor for the B–cell activation antigen B7," *J. Exp. Med.* 174:561–569 (1991).
Kaufman et al., "Cysteines in the Transmembrane Region of Major Histocompatibility Complex Antigens Are Fatty Acylated via Thioester Bonds," *J. Biol. Chem.* 259:7230–7238 (1984).
Rose et al., "The presence of cysteine in the cytoplasmic domain of the vesicular stomatitis virus glycoprotein is required for palmitate addition," *Proc. Natl. Acad. Sci. USA* 81:2050–2054 (1984).
Lemke et al., "Isolation and Analysis of the Gene Encoding Peripheral Myelin Protein Zero," *Neuron* 1:73–83 (1988).
Littman et al., "Unusual intron in the immunoglobulin domain of the newly isolated murine CD4 (L3T4) gene," *Nature* 325:453–455 (1987).
Owens et al., "Organization of the neural cell adhesion molecule (N–CAM) gene: alternative exon usage as the basis for different membrane–associated domains," *Proc. Natl. Acad. Sci. USA* 84:294–298 (1987).
Kasinrerk et al., "Human Leukocyte Activation Antigen M6, A Member of the Ig Superfamily . . . ," *Journ. of Immunol.* 149:847–854 (1992).
Wang et al., "Identification and Molecular Cloning of Tactile . . . ," *Journ. of Immunol.* 148:2600–2608 (1992).
Brunet et al., "A Differential Molecular Biology Search for Genes Preferentially Expressd in Functional T Lymphocytes . . . ," *Immunol. Reviews*, No. 103, pp. 22–36 (1988).

(List continued on next page.)

*Primary Examiner*—Paula K. Hutzell
*Assistant Examiner*—Heather A. Bakalyar
*Attorney, Agent, or Firm*—Weingarten, Schurgin, Gagnebin & Hayes LLP

[57] ABSTRACT

HB15-related lymphocyte activation antigens, and nucleic acid sequences encoding HB15-related antigens are disclosed. Also disclosed are antibodies reactive with HB15.

8 Claims, 17 Drawing Sheets

OTHER PUBLICATIONS

Zhou et al., "A Novel Cell–Surface Molecule Expressd by Human Interdigitating Reticulum . . . ," *Journ. of Immunol.* 149:735–742 (1992).

King et al., "Mechanisms of Dendritic Cell Function," Bland–Sutton Institute, University College and Meddlesex School of Medicine 11(6) (1990).

Steinman, "The Dendritic Cell System and its Role in Immunogenicity," *Annu. Rev. Immunol.* 9:271–296 (1991).

Streilein et al., "Functional Dichotomy between Langerhans Cells that Present Antigen to Naive . . . ," *Immunol. Reviews* 117:160–183 (1990).

EMBL Database entry EBV, accession no V01555 et al.; 1983; Epstein–Barr virus genome. *sequence*.

```
gaattcCGCC ATG TCG CGC GGC CTC CTC CTG CAG CTC CTC CTG AGC TGC GCC TAC AGC CTG GCT    61
            M   S   R   G   L   L   L   Q   L   L   L   S   C   A   Y   S   L   A
            1                               10
P   A   T   ACG GCG CCG GAG GTG AAG GTG GCT TGC TCC GAA GAT GTG GAC TTG CCC TGC ACC GCC    121
P   A   T   T   A   P   E   V   K   V   A   C   S   E   D   V   D   L   P   C   T   A
    20                                          31
P   W   D   P   Q   V   P   Y   T   V   S   W   V   K   L   T   T   L   E   G   G   E   181
CCC TGG GAT CCG CAG GTT CCC TAC ACG GTC TCC TGG GTC AAG TTG ACG ACG TTG GAG GGT GGT GAA
    40                              +       50
E   R   M   E   T   P   Q   E   Q   E   H   L   R   G   Q   H   Y   H   Q   K   G   241
GAG AGG ATG GAG ACA CCC CAG GAG CAG GAA CAC CTC AGG GGA CAG CAC TAT CAT CAG AAG GGG
    60                              70
Q   N   G   S   F   D   A   P   N   E   R   P   Y   L   Q   I   R   N   T   301
CAA AAT GGT TCT TTC GAC GCC CCC AAT GAA AGG CCC TAT CTG CTG AAG ATC CGA AAC ACT
    80                              90                      +       +
T   S   N   G   K   C   T   Y   R   T   G   T   G   C   Q   D   P   Q   R   N   361
ACC AGC AAT GGC AAG TGC ACA TAC AGG ACT GGA ACA GGA TGC CAG GAT CCG CAG AGA AAC
    100                             110                     120
L   S   G   K   V   I   L   R   V   L   L   V   L   A   Q   L   E   K   E   T   421
CTA AGT GGC AAG GTG ATC TTG AGA GTG GTG CTG GTC CTG GCA CAG CTG GAA AAA GAG ACT
120                                 130                             140
F   K   Y   K   A   E   A   F   L   P   V   T   F   Y   L   T   481
TTT AAG TAC AAA GCA GAA GCG TTT CTC CCA GTT ACC TTC TAC TTA ACA
                                150
L   I   F   T   C   K   F   A   R   L   Q   S   I   F   P   D   F   S   K   541
CTC ATC ATT TTC ACT TGT(AAG)TTT GCA CGG CTA CAG AGT ATC TTC CCA GAT TTT TCT AAA
                                160                 170
A   G   M   E   R   A   F   L   P   V   T   S   P   N   K   H   L   G   L   V   601
GCT GGC ATG GAA CGA GCT TTT CTC CCA GTT ACC TCC CCA AAT AAG CAT TTA GGG CTA GTG
```

*FIG. 2A*

```
        180                   H    K    T    E    L    *
         P    H    K    T    E    L    V                                                         186
ACT CCT CAC AAG ACA GAA CTG GTA TGA GCAGGATTTC TGCAGGTTCT TCTTCCTGAA GCTGAGGCTC                   668
AGGGGTGTGC CTGTCTGTTA CACTGGAGGA GAGAAGAATG AGCCTACGCT CCATTTTCTG GAAGATGGCA TCCTGTGAAG         738
TCCTTCACCT CACTGAAAAC ATCTGGAAGG GGATCCCACC TGGCCAGGCC TCGAAAACCA                                808
TCACATGACC ACATAGCATG AGGCCACTGC TGCTTCTCCA TGGCCACCTT TTCAGCGATG TATGCAGCTA                     878
TCTGGTCAAC CTCCTGGACA TTTTTTCAGT CATATAAAAG CTAGGTGAG ATGCAGCTGG AAAAGGTCT                       948
TGGGAAATAT GAATGCCCCC AGCTGGCCCG TGACAGACTC CTGTCCTCTT CTGCATCTTG                               1018
GGGACATCTC TTTGAATTTT CTGTGTTTTG CTGTACCAAG TACGTCTGGG AGAAATTGAC                               1088
AGATCAAGCT GTGAGACAGT GGGAAATATT CCAGATGTTT GCTATTACTA                                          1158
AGGAGTAATC TGTGTACAAA GAAATAACAA GTCGATGAAC TTTCCTGGTG TCATCTGGGA                               1228
AAGACATCCA TAAAGAAGCA ATAAAGAAGA GTGCCACATT CAGGGTCTTT CTTGTCAAAG                               1298
AAGGTTTGTG TTTTTCTGCT TTTGAAATCT TATTTTTATA ACAGGCAGCC                                          1368
TGGACATAGA GAGGGAGAAG AAGTCAGAGA ATAGAGAGCT TGTGAACTG ATTAATGGC                                 1438
TGCTGGGCTG ACGGTGCAGT CTGGGTGCTC GTCCACTTGT CCCACTATCT GGGTGCATGA TCTTGAGCAA                    1508
GTTCCTTCTG GTGTCTGCTT TCTCCATTGT AAACCACAAG CTATACAGAT GGGCTAATGA AGATCATATA                    1578
CGTGAAAATT CTTTGAAAAC ATATAAAGCA ATGAGAGGGT TCGAAACTCC ATTGAGTCAT TATCCTTGCT                    1648
ATGATGATGG TGTTTTGGGG ATGAGAGGGT GCTATCCATT TCTCATGTTT TCCATTGTGT                               1718
AGGTTACCAA GAAGCCTTTC CTGTAGCCTT CTGTAGGAAT TCC                                                 1761
```

FIG. 2B

COMPARISON BETWEEN HUMAN AND MOUSE HB15 cDNA SEQUENCES

```
m   ACCCACGCG  TcCgCccAcgcGTC  CGGTGTCGCAG h   gaattcCGCC  ATG  TCG  CGC  GGC  CTC  CAG  CTT  CTC  CTG  AGC  TGC  GCC  TAC  AGC  CTG  GCT    61
m   CGCTCCAGCC  ATG  TCG  CAA  GGC  CTC  CTG  TTT  CTA  GGC  TGC  TGC  GCT  gcc  tgg  cac  cgc M    S    R    G    L    Q    L    L    L    S    C    A    Y    S    L    A
         1                                              10
    P    A  ^ T    P    E    V    K    V    A    C    S    E    D    V    D    L    P    C    T    A
h   CCC  GCG   ACG  CCG  GAG  GTG  AAG  GTG  GCT  TGC  TCC  GAA  GAT  GTG  GAC  TTG  CCC  TGC  ACC  GCC   121
m   gat  ggc   gat  gtg  gag  gtg  acg  gtg  gct  tcc  gag  acT  TGC  TGC  CCT  TGC  ACA  GCG
                                                          31
         D            V                                    V
                 20                                                      +
    P    D    P    Q    V    P    Y    T    V    S    W    V    K    L    L    E    G    G    E
h   CCC  GAT  CCG  CAG  GTT  CCC  TAC  ACG  GTC  TCC  TGG  GTC  AAG^TTA  TTG  GAG  GGT  GGT  GAA   181
m   CCC  GAC  CCG  CAG  GAC  CTC  TAT  GCA  GTG  TCC  TGG  GCC  AAG^---  ---  ---  ---  ---  ---
         *                               **        ***   ***    *

E    R    M    E    T    P    Q    E    D    H    L    R    A    G    Q    H    Y    Q    K    G
h   GAG  AGG  ATG  GAG  ACA  CCC  CAG  GAA  GAC  CAC  CTC  AGG  GCA  GGA  CAG  CAC  TAT  CAG  AAG  GGG  241
m   ---  ---  ---  GTC  GAG  AGT  GAG  ACT  GGC  GAG  CTC  CCG         GGA  GTG  GAG  CTC  CCG  AGC  AAG
                                                                       **           *

70               +
    Q    G    S    F    D    A    P    N    E    R    P    Y    S    L    K    I    R    N    T
h   CAA  GGT  TCT  TTC  GAC  GCC  CCC  AAT  GAA  AGG  CCC  TAT  TCC  CTG  AAG  ATC  CGA  AAC  ACT   301
m   CAA  AGC  TCC  TTC  GAG  GCC  CCC  AAC  AGA  AGG  CCC  TAT  TCC  CTG  ACG  ATC  CAA  AAC  ACT
                 *        *             *         *                        *        *        ***

60
         N    G                                              L
                 80                                       90
    T    S    C    N    S    Y    G    T    Y    R    C    T    L    Q    D    P    D    G    Q    R    N
h   ACC  AGC  TGC  AAC  TCG  GGG  ACA  TAC  AGG  TGC  ACT  CTG  CAG  GAC  CCG  GAT  GGG  CAG  AGA  AAC   361
m   ACC  ATC  TGC  AGC  TCG  GGC  ACC  TAC  AGG  TGT  GCC  CTG  CAG  GAG  CTC  GGA  GGG  CAG  CGC  AAC
         *        *             *             *        ***        *        *
```

FIG. 6A

```
       L    S    G    K    V    I    L    R    V    T    G    C    P    A    Q    R    K    E    T
                 100                                110
h CTA AGT GGC AAG GTG ATC TTG AGA GTG ACA G^GA TGC CCT GCA CAG CGT AAA GAA GAG ACT  421
m TTG AGC GGC ACC GTG GTT CTG AAG GTG ACA G^GA TGC CCC AAG GAA GAG TCA ACT
   ***  *  ***  **  ***  *   *   **  ***  *** ***  *   **  *** *   ***  *           ***

F    K    K    Y    R    A    E    I    V    L    L    A    L    V    I    F    Y    L    T
                 120                                130
h TTT AAG AAA TAC AGA GCG GAG ATT GTC CTG CTG GCT CTG GTT ATT TTC TAC TTA ACA  481
m TTC AGG AAG TAC AGG GCA GAA GCT GTG TTG TTC TCT CTG GTT TAC TAC CTG ACA
   **   *   *  ***  *  **  **   *  **  *    *       ***  **  *** ***  *           ***

L    I    I    F    T    C    K    F    A    R    L    Q    S    I    F    P    D    F    S    K
                 140                                150
h CTC ATC ATT TTC ACT TGT^AAG TTT GCA CGG CTA CAG AGT ATC TTC CCA GAT TTT TCT AAA  541
m CTC ATC ATT TTC ACC TGC AAA TTT GCA CGA CTA CAA AGC ATT TTC CCA GAT ATT TCT AAA
   *** *** *** *** **  *   *  ***  **  *   *** *   *   *  ***  **   **   **  ***    ***

A    G    M    E    R    A    F    L    P    V    T    S    P    N    K    H    L    G    L    V
                 160                                170
h GCT GGC ATG GAA CGA GCT TTT CTC CCA GTT ACC TCC CCA AAT AAG CAT TTA GGG CTA GTG  601
m CCT GGT ACG GAA CAA GCT CTT CTT CCA GTC ACC TCC CCA AGC AAA CAT TTG GGG CCA GTG
   *    *    *  ***    *  ***   *   *  ***  *   ***  **    *   *   ***  *  ***         ***

T    P    H    K    T    E    L    V
                 180                 186
h ACT CCT CAC AAG ACA GAA CTG GTA TGA GCAGGATTTC TGCAGGTTCT TCTTCCTG-A AGCTGAGGCT  668
m ACC CTT CCT AAG ACA GAA ACG GTA TGA GTAGGATCTC CACTGGTTTT TACAAAGCCA AGGGCACA-T
   **   *    *  *  *  **    * * *  * *      * ****         *  *     * *            * h CAGGG--GTG TGCCTGTCTG TTACACTGGA GGAGAGAAGA ATGAGCCTAC GCTGAAGATG GCATCCTGT-  738
m CAGATCAGTG TGCCTGAATG CCACCC-GGA CAAGAGAAGA ATGAGCTCCA TCCTCAGATG GCAACCTTTC
   ***     ***  ******  *       **     *******  ******        *  *****  **  ****  *
```

FIG.6B

```
h  TTTGAAGTCC TTCACCTCAC TGAAAACATC TGGAAGGGGA TCCCACCCCA TTTTCTGTGG GCAGGCCTCG
m  ---GAAGTCC TTCACCTGAC AG-------- TGGGCTCC-A CACTACTCCC -TGACACAGG GTCTTGAGC-
   ******  *****           ****** *  *  *  ***** ****** h  AAAACCATCA CATGACCACA TAGCATG-AG GC-CACTGCT GCTTCTCCAT GGCCACCTTT TCAGCGATGT ATGCAGCTA
m  ---ACCATCA TATGATCACG AAGCATGGAG TATCACCGCT TCTCTGTGCT GTC-AGCTTA --AT-GTTTC ATGTGGCTA   948
      ****** * *  * ***  *  *** * *   * ****  *  *****    * * *  * **** h  TCTGGTCAAC CTCCTGGACA TTTTTTCAGT CATATAAAAG CTATGGTGAG ATGCAGCTGG AAAAGGGTCT
m  TCTGGTCAAC CTCGTG-AGT GCTTTTCAGT CATCTACAAG CTATGGTGAG ATGCAGGTGA AGCAGGTCA   1018
   ******** * ** * * ******* *  * ******** **   *  *** * h  TGGGAAATAT GAATGCCCCC AGCTGGCCC-G TGACAGACTC CTGAGGACAG CTGTCCTCTT CTGCATCTTG
m  TGGGAAATTT GAACACTCTG AGCTGGCCCTG TGACAGACTC CTGAGGACAG CTGTC-TCTC CTACATCTGG   1088
   ******** * ***  *  *  ********* * ******** ****** *  *  * **** * h  GGGACATCTC TTTGAATTTT CTGTGTTTTG CTGTACCAGC CCAGATGTTT TACGTCTGGG AGAAATTGAC
m  GATACATCTC TTTGAATTTG TCCTGTTTCG TTGCACCAGC CCAGATGTCT CACATCTGGC GGAAATTGAC   1158
   * ******* ******  * ****** *  * *****  ****** *   *  **   ***** h  AGATCAAGCT GTGAGACAGT GGGAAATATT TAGCAAATAA TTTCCTGGTG TGAAGGTCCT GCTATTACTA
m  AGGCCAAGCT GTGAGCCAGT GGGAAATATT TAGCAAATAA TTTCCAGTGG CGAAGGTCCT GCTATTAGTA   1228
     *  *  ****** ****** ***  * * ********* **** h  AGGAGTAAATC TGTGTACAAA GAAATAACAA GTCGATGAAC TATTCCCCAG CAGGGTCTTT TCATCTGGGA
m  AGGAGTATTA TGTGTACATA GAAATGAGAG GTCAGTGAAC TATTCCCCAG CAGGGCCTTT TCATCTGGAA   1228
   *******  * ******** * *****  *  * *** ***** ********** ****** *** ********* *
```

FIG. 6C

```
h AAGACATCCA TAAA-GAAGCA ATAAAGAAGA GTGCCA-CATT TATTTTT-ATA TCTATATGTA CTTGTCAAAG    1298
m AAGACATCCA CAAAAGCAGCA ATACAGAGGG ATGCCAGCATT TATTTTTTAA TCTTCATGTA -TTGTCAAAG
  ********   * *  *** ** * ******* * *  *  ******* h AAGG-TTTGT ---GTTTTT- CTGCTTTTGA AATCTGTATC TGTAGTGAGA TAGCATTGTG AA-CTG-ACA
m AAGAATTTTT CATGTTTTTT CAAA---GA AGTGTGTTTC TTTCCTTTTT TAAAATA-TG AAGGTCTAGT
  *  **  *  ******  * *    *  * * *  *   * * * *  **  *   * h --GGCAGCCTGGACATAGAGAGG ------GAGAAGAAG TCAGAGA-GGGTGA CAAGATAGAG AGCTATTTAA
m TACATAGCATTGCTACGTACAAG CAGCCTGAGA-GAAG ATGGAGAATGTTCCT CAAAATAGGG ACAGCAAGCT
      ****  *     * **       * * **** *       *  * * ** *   * *  * * h TGGCCCGGCTGGAAA
m AGAACGACTGTACA
   *  *    * h -TGCTGGGCTG ACGGT GCAGTC     TGG GTGCTC GTCCACTGT      CCCACTATC TGGG-TGCATGAT-CTTGAGCAA
m GTGCCT-GCTG GGAAGGGCAGAC AATGGACTGAGA AACCAGAAGT CTGGCCACAAGA TTGTCTGTATGATTCTGGACGA-    1578
  *   **  * *   **            **   *        ***  * ** * * *  *  * h GTTCCTTCTG GTGTCTGCTT TCTCCATTGT AAACCACAAG GCTGTTGCAT GGGCTAATGA AGATCATATA
m GTCACTTGTG GTTTTCACTC TCTGGTTAGT AAACCAGATA GTT TAGTCT GGG T TGA ATACAATGA        1648
  ** *   ** * * *  ***  * *  **** *   * *    **   * *** *  ** h CGTGAAAATT CTTTGAAAAC ATATAAAGCA CTATACAGAT TCGAAACTCC ATTGAGTCAT TATCCTTGCT
m TGTGAAGTTG CTTGGGGAAA GCTGAATGTA GTGAATACAT TGCAACTCT ACTGGGCTGT TA CCTGTTG       1718
  ***** *    *** * *** * *  * * * * ***** * *     *    *  ** * * * h ATGATGATGG TGTTTTGGGG ATGAGAGGGT GCTATCCATT TCTCATGTTT GAAACAAAGA
m AT ATCCTAG AGTTCTGGAG CTGAGACGATCGCTGCTTG TCTCAGCTTG CCCATCAATC CAAACACAGG
  ** * *  *  * *    * ** *      *** * *   * *   *  *   * *** h AGGTTACCAA GAAGCCTTTC CTGTAGCCTT CTGTAGGAAT TCCTTTTGGG GAAGTGAGGA AGCCAGTGCC    1788
m AGGCTACAAA AAGGACATGA GCATGGTCTT CTGTGTGAAC TCCTCCT GA GAAACGTGG AGACTGGCTC
  ***  ** ** * * ** *   *  *  * ** **** * * * **** **     *    ** * ** * ** *
```

*FIG. 6D*

```
h A-CGGTCTGT TCTTGAAGCA GTAGCC-TAA CACACTCCAA GATATGGACA CACGGGAGCC GCTGGGC-A-    1858
m AGCGCTTTGT GCTCGAAGGA CTAATCACAA GTTCTTCGAA GATATGGACC TAGGGGAGCT ATTGCGCCAC
  *  **    ***  *   **  *       * *  ********  *  *******   *  **   * ** h GAAGGGAC-- -TTCACGAAG GTTTGCATGG ATGTTTTAGC CATTGTTGGC TTTCCCTTAT CAAACTTGGGCCCT  1928
m GACAGGAGGA AGTTCTCAGA TGTTGCATTG ATG--TAA-- CATTGTTGCA TTTCTTTAAT GAG-CTGGGCTCCT
  *   *    ****    ***     *      ******  ***  *  *   ****** * *** h TCCCTTCTTG GTTTCCAAAG GCATTTTATT GCTTGAGTTA T-ATGTTCAC TGTCCCCTAATATTAGGGA  1998
m TCCTCATTTG CTTCCCAAAG AGATTTT--- GTCCCACTAA TGGTGTGCCC ATCACCACTATGAAAA-
  *** *  * ****** *     ****     *    *    * *** *  *   *    * h GTAAAACGGA TACCAAGTTG ATTTAG--TG TTTTTACCTC T---GTCTT- GGCTTTCATG TTATTAAACT
m GTAAAAGGGA TGCTGAGCAG ATACAGGCTA GTCTTACCTC TCAAGTCCAT GACTTTCATG CTATTAAA--
  **** * *    **  *   ** * * *******  *    ***  * ******  ***** h GA-TGCATGTG AAGAAAGGGT GTTTTCTGT TTTATATTCA ACTCATAAG ACTTTGGGATA GGAAAAATGA
m GAATGCATGTG AAG-AGTGT GTTCTCTTT TCTATCTTTA AAATGATCG ACTTAGAGTG AGTGTTTGGG
   **** * *   *   * *** * ** *   *   * *  *   * h GTAATGGTTA CTAGGCTTA -ATACCTGGGTG ATTACA    TAATCTGTACAAT GAACCCCCATG --ATGT  2208
m TGCTGAGTG GAGAG-TAA GAATGCAGAAATGGTAGTGG TAAA-TGACTGGC TGCTTCCCGAGG AGTGTTTGGG  GGATCC h AAGTTTACCTATGTAA CAAACCTGCA CTTATACCCA TGAACTTAAA ATGAAAGTTA AAAATAAAAA ACATATACAA A   2269
```

*FIG. 6E*

HUMAN AND MOUSE HB15 OLIGONUCLEOTIDES

```
       M   S   R   G   L   Q   L   L   L   L   S   C   A   Y   S   L   A
h gaattcCGCC ATG TCG CGC GGC CTC CAG CTC CTC CTG CTC AGC TGC GCC TAC AGC CTC CCT   61
m CGcTCCAGCC ATG TCG CAA gGC CTC CAG CTC CTG CTG CTT CTA GGC TGC GCT gcc cgc cac cgc
                                                                    ======> LJZ001

==================================================================> 2087
       P   A^  T   P   E   V   K   V   A   C   S   E   D   V   D   L   P   C   T   A
h    CCC GCG ACG CCG GAG GTG AAG GTG GCT TGC TCC GAA GAT GTG GAC TTG CCC TGC ACC GCC   121
m    gat ggc gat gtg gag gtg acg gtg gct tgc tcc gag acT gcc gAC TTG CCT TGC ACA GCG <============== 2086
                       P   Y   T   V   S   W   V   K   L   L   E   G   G   E
h    CCC GAT CCG CAG GTT CCC TAC ACG GTC TCC TGG GTC AAG^TTA TTG GAG GGT GGT GAA   181
m    CCC GAC CCG CAG GTT CTC TCC TAT GCA GTG TCC TGG GCC AAG^ --- --- --- --- ---

==============================> 2085
       E   R   M   E   T   P   Q   E   D   H   L   R   G   Q   H   Y   H   Q   K   G
h    GAG AGG ATG GAG ACA CCC CAG GAA GAC CAC CTC AGG GGA CAG CAC TAT CAT CAG AAG GGG   241
m    --- --- --- --- GTC GAG AGT GGC ACT GAG GTG CTC CCG GAG AGC AAG ---

Q   N   G   S   F   D   A   P   N   E   R   P   Y   S   L   K   I   R   N   T
h    CAA AAT GGT TCT TTC GAC GCC CCC AAT GAA AGG AGG CCC TAT TCC CTG AAG ATC CGA AAC ACT   301
m    CAA AAC AGC TCC TTC GAG GCC GCC CCC AGG AGA AGG GCC TAT TCC CTG ACG ATC CAA AAC ACT
```

*FIG. 7A*

```
         T   S   C   N   S   G   T   Y   R   C   T   L   Q   D   P   D   G   Q   R   N       <=
      h ACC AGC TGC AAC TCG GGG ACA TAC AGG TGC ACT CTG CAG GAC CCG GAT GGG CAG AGA AAC      361
      m ACC ATC TGC AGC TCG GGC ACC TAC AGG TGT GCC CTG GAG CAG CCG GGA GGG CAG CGC AAC
        ============================================> 2406    ===============> 2083
        ============================================= 2489                    <==
                                                                               E   T
         L   S   G   K   V   I   L   R   V   T   G   C   P   A   Q   R   K   E   E   T
      h CTA AGT GGC AAG GTG ATC TTG AGA GTC ACA G^GA TGC CCT GCA CAG CGT AAA GAA GAG ACT    421
      m TTG AGC GGC ACC GTG CTG CTG AAG GTG ACA G^GA TGC CCC AAG GAA GCT ACA GAG TCA ACT
                                                       <================= TFT617
                                                       <================= LJ33
         F   K   Y   R   A   E   I   V   L   L   L   A   L   V   I   F   P   D   F   S   K
      h TTT AAG TAC AGA GCG GAG ATT GTC CTG CTG CTG GCT CTG GTT ATC TTC CCA GAT TTT TCT AAA 541
      m TTC AAG TAC AGG GCA GAA GCT GTC GTG TTG CTC CTC CTG GTT ATT TTC CCA GAT TCT AAA
                                   <================= 2082
         L   I   I   F   T   C   K   F   A   R   L   Q   S   I   F   P   Y   L   T
      h CTC ATC ATT TTC ACT TGT^AAG TTT GCA CGG CTA CAG AGT ATC TTC CCA TAT TTA ACA         541
      m CTC ATC ATT TTC ACC TGC AAA TTT GCA CGA CTA CAA AGC ATT TTC CCA TAC CTG ACA
        =================> 2084                                          <== L   T
         L   I   F   T   C   K   F   A   R   L   Q   S   I   F   Y   L   T
         A   G   M   E   D   A   F   F   L   P   V   T   S   P   N   K   H   L   G   V
      h GCT GGC ATG GAA GAT GCT TTT CTC CCA GTT ACC TCC CCA AAT AAG CAT TTA GGG CTA GTG     601
      m CCT GGT ACG GAA CGA GCT GCT CTT CCT GTC ACC TCC CCA AGC AAA CAT TTG GGG CCA GTG
                                                                             = 2407
         T   P   H   K   T   E   L   V   *
      h ACT CCT CAC AAG ACA GAA CTG GTA TGA
      m ACC CTT CCT AAG ACA GAA ACG GTA TGA
                                 <==
```

*FIG. 7B*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 2272 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 11..625

( x i ) SEQUENCE DESCRIPTION: SEQ ID NO:1:

```
GAATTCCGCC ATG TCG CGC GGC CTC CAG CTT CTG CTC CTG AGC TGC GCC        49
           Met Ser Arg Gly Leu Gln Leu Leu Leu Leu Ser Cys Ala
            1               5                  10

TAC AGC CTG GCT CCC GCG ACG CCG GAG GTG AAG GTG GCT TGC TCC GAA        97
Tyr Ser Leu Ala Pro Ala Thr Pro Glu Val Lys Val Ala Cys Ser Glu
     15              20                  25

GAT GTG GAC TTG CCC TGC ACC GCC CCC TGG GAT CCG CAG GTT CCC TAC       145
Asp Val Asp Leu Pro Cys Thr Ala Pro Trp Asp Pro Gln Val Pro Tyr
 30              35                  40                  45

ACG GTC TCC TGG GTC AAG TTA TTG GAG GGT GGT GAA GAG AGG ATG GAG       193
Thr Val Ser Trp Val Lys Leu Leu Glu Gly Gly Glu Glu Arg Met Glu
                 50                  55                  60
```

-continued

```
ACA CCC CAG GAA GAC CAC CTC AGG GGA CAG CAC TAT CAT CAG AAG GGG      241
Thr Pro Gln Glu Asp His Leu Arg Gly Gln His Tyr His Gln Lys Gly
            65                  70                  75

CAA AAT GGT TCT TTC GAC GCC CCC AAT GAA AGG CCC TAT TCC CTG AAG      289
Gln Asn Gly Ser Phe Asp Ala Pro Asn Glu Arg Pro Tyr Ser Leu Lys
        80                  85                  90

ATC CGA AAC ACT ACC AGC TGC AAC TCG GGG ACA TAC AGG TGC ACT CTG      337
Ile Arg Asn Thr Thr Ser Cys Asn Ser Gly Thr Tyr Arg Cys Thr Leu
        95                 100                 105

CAG GAC CCG GAT GGG CAG AGA AAC CTA AGT GGC AAG GTG ATC TTG AGA      385
Gln Asp Pro Asp Gly Gln Arg Asn Leu Ser Gly Lys Val Ile Leu Arg
110                 115                 120                 125

GTG ACA GGA TGC CCT GCA CAG CGT AAA GAA GAG ACT TTT AAG AAA TAC      433
Val Thr Gly Cys Pro Ala Gln Arg Lys Glu Glu Thr Phe Lys Lys Tyr
                130                 135                 140

AGA GCG GAG ATT GTC CTG CTG CTG GCT CTG GTT ATT TTC TAC TTA ACA      481
Arg Ala Glu Ile Val Leu Leu Leu Ala Leu Val Ile Phe Tyr Leu Thr
                145                 150                 155

CTC ATC ATT TTC ACT TGT AAG TTT GCA CGG CTA CAG AGT ATC TTC CCA      529
Leu Ile Ile Phe Thr Cys Lys Phe Ala Arg Leu Gln Ser Ile Phe Pro
        160                 165                 170

GAT TTT TCT AAA GCT GGC ATG GAA CGA GCT TTT CTC CCA GTT ACC TCC      577
Asp Phe Ser Lys Ala Gly Met Glu Arg Ala Phe Leu Pro Val Thr Ser
175                 180                 185

CCA AAT AAG CAT TTA GGG CTA GTG ACT CCT CAC AAG ACA GAA CTG GTA      625
Pro Asn Lys His Leu Gly Leu Val Thr Pro His Lys Thr Glu Leu Val
190                 195                 200                 205

TGAGCAGGAT TTCTGCAGGT TCTTCTTCCT GAAGCTGAGG CTCAGGGGTG TGCCTGTCTG     685
TTACACTGGA GGAGAGAAGA ATGAGCCTAC GCTGAAGATG GCATCCTGTT TTGAAGTCCT     745
TCACCTCACT GAAAACATCT GGAAGGGGAT CCCACCCCAT TTTCTGTGGG CAGGCCTCGA     805
AAACCATCAC ATGACCACAT AGCATGAGGC CACTGCTGCT TCTCCATGGC CACCTTTTCA     865
GCGATGTATG CAGCTATCTG GTCAACCTCC TGGACATTTT TTCAGTCATA TAAAAGCTAT     925
GGTGAGATGC AGCTGGAAAA GGGTCTTGGG AAATATGAAT GCCCCAGCT GGCCCGTGAC      985
AGACTCCTGA GGACAGCTGT CCTCTTCTGC ATCTTGGGGA CATCTCTTTG AATTTTCTGT    1045
GTTTTGCTGT ACCAGCCCAG ATGTTTTACG TCTGGGAGAA ATTGACAGAT CAAGCTGTGA    1105
GACAGTGGGA AATATTTAGC AAATAATTTC CTGGTGTGAA GGTCCTGCTA TTACTAAGGA    1165
GTAATCTGTG TACAAAGAAA TAACAAGTCG ATGAACTATT CCCCAGCAGG GTCTTTTCAT    1225
CTGGGAAAGA CATCCATAAA GAAGCAATAA AGAAGAGTGC ACATTTATT TTTATATCTA     1285
TATGTACTTG TCAAAGAAGG TTTGTGTTTT TCTGCTTTTG AAATCTGTAT CTGTAGTGAG    1345
ATAGCATTGT GAACTGACAG GCAGCCTGGA CATAGAGAGG GAGAAGAAGT CAGAGAGGGT    1405
GACAAGATAG AGAGCTATTT AATGGCCGGC TGGAAATGCT GGGCTGACGG TGCAGTCTGG    1465
GTGCTCGTCC ACTTGTCCCA CTATCTGGGT GCATGATCTT GAGCAAGTTC CTTCTGGTGT    1525
CTGCTTTCTC CATTGTAAAC CACAAGGCTG TTGCATGGGC TAATGAAGAT CATATACGTG    1585
AAAATTCTTT GAAAACATAT AAAGCACTAT ACAGATTCGA AACTCCATTG AGTCATTATC    1645
CTTGCTATGA TGATGGTGTT TTGGGGATGA GAGGGTGCTA TCCATTTCTC ATGTTTTCCA    1705
TTGTTTGAAA CAAAGAAGGT TACCAAGAAG CCTTTCCTGT AGCCTTCTGT AGGAATTCCT    1765
TTTGGGGAAG TGAGGAAGCC AGGTCCACGG TCTGTTCTTG AAGCAGTAGC CTAACACACT    1825
CCAAGATATG GACACACGGG AGCCGCTGGG CAGAAGGGAC TTCACGAAGG TTTGCATGGA    1885
TGTTTTAGCC ATTGTTGGCT TTCCCTTATC AAACTTGGGC CCTTCCCTTC TTGGTTTCCA    1945
```

```
AAGGCATTTT  ATTGCTTGAG  TTATATGTTC  ACTGTCCCCC  TAATATTAGG  GAGTAAAACG    2005

GATACCAAGT  TGATTTAGTG  TTTTTACCTC  TGTCTTGGCT  TTCATGTTAT  TAAACTGATG    2065

CATGTGAAGA  AAGGGTGTTT  TTCTGTTTTA  TATTCAACTC  ATAAGACTTT  GGGATAGGAA    2125

AAATGAGTAA  TGGTTACTAG  GCTTAATACC  TGGGTGATTA  CATAATCTGT  ACAATGAACC    2185

CCCATGATGT  AAGTTTACCT  ATGTAACAAA  CCTGCACTTA  TACCCATGAA  CTTAAAATGA    2245

AAGTTAAAAA  TAAAAAACAT  ATACAAA                                          2272
```

( 2 ) INFORMATION FOR SEQ ID NO:2:

( i ) SEQUENCE CHARACTERISTICS:
    ( A ) LENGTH: 205 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Ser Arg Gly Leu Gln Leu Leu Leu Ser Cys Ala Tyr Ser Leu
 1           5                  10                 15

Ala Pro Ala Thr Pro Glu Val Lys Val Ala Cys Ser Glu Asp Val Asp
            20                 25                 30

Leu Pro Cys Thr Ala Pro Trp Asp Pro Gln Val Pro Tyr Thr Val Ser
        35                  40                 45

Trp Val Lys Leu Leu Glu Gly Gly Glu Arg Met Glu Thr Pro Gln
     50                  55                 60

Glu Asp His Leu Arg Gly Gln His Tyr His Gln Lys Gly Gln Asn Gly
 65              70                 75                 80

Ser Phe Asp Ala Pro Asn Glu Arg Pro Tyr Ser Leu Lys Ile Arg Asn
                 85                 90                 95

Thr Thr Ser Cys Asn Ser Gly Thr Tyr Arg Cys Thr Leu Gln Asp Pro
             100                105                110

Asp Gly Gln Arg Asn Leu Ser Gly Lys Val Ile Leu Arg Val Thr Gly
         115                120                125

Cys Pro Ala Gln Arg Lys Glu Glu Thr Phe Lys Lys Tyr Arg Ala Glu
     130                135                140

Ile Val Leu Leu Leu Ala Leu Val Ile Phe Tyr Leu Thr Leu Ile Ile
145                 150                155                160

Phe Thr Cys Lys Phe Ala Arg Leu Gln Ser Ile Phe Pro Asp Phe Ser
                 165                170                175

Lys Ala Gly Met Glu Arg Ala Phe Leu Pro Val Thr Ser Pro Asn Lys
             180                185                190

His Leu Gly Leu Val Thr Pro His Lys Thr Glu Leu Val
         195                200                205
```

( 2 ) INFORMATION FOR SEQ ID NO:3:

( i ) SEQUENCE CHARACTERISTICS:
    ( A ) LENGTH: 2197 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:

(A) NAME/KEY: CDS
(B) LOCATION: 45..626

(xi) SEQUENCE DESCRIPTION: SEQ ID NO:3:

```
ACCCACGCGT CCGCCCACGC GTCCGGTGTC GCAGCGCTCC AGCC ATG TCG CAA GGC        56
                                                   Met Ser Gln Gly
                                                    1

CTC CAG CTC CTG TTT CTA GGC TGC GCT GCC TGG CAC CGC GAT GGC GAT        104
Leu Gln Leu Leu Phe Leu Gly Cys Ala Ala Trp His Arg Asp Gly Asp
 5               10                  15                  20

GTG GAG GTG ACG GTG GCT TGC TCC GAG ACT GCC GAC TTG CCT TGC ACA        152
Val Glu Val Thr Val Ala Cys Ser Glu Thr Ala Asp Leu Pro Cys Thr
             25                  30                  35

GCG CCC TGG GAC CCG CAG CTC TCC TAT GCA GTG TCC TGG GCC AAG GTC        200
Ala Pro Trp Asp Pro Gln Leu Ser Tyr Ala Val Ser Trp Ala Lys Val
         40                  45                  50

TCC GAG AGT GGC ACT GAG AGT GTG GAG CTC CCG GAG AGC AAG CAA AAC        248
Ser Glu Ser Gly Thr Glu Ser Val Glu Leu Pro Glu Ser Lys Gln Asn
     55                  60                  65

AGC TCC TTC GAG GCC CCC AGG AGA AGG GCC TAT TCC CTG ACG ATC CAA        296
Ser Ser Phe Glu Ala Pro Arg Arg Arg Ala Tyr Ser Leu Thr Ile Gln
 70                  75                  80

AAC ACT ACC ATC TGC AGC TCG GGC ACC TAC AGG TGT GCC CTG CAG GAG        344
Asn Thr Thr Ile Cys Ser Ser Gly Thr Tyr Arg Cys Ala Leu Gln Glu
 85                  90                  95                 100

CTC GGA GGG CAG CGC AAC TTG AGC GGC ACC GTG GTT CTG AAG GTG ACA        392
Leu Gly Gly Gln Arg Asn Leu Ser Gly Thr Val Val Leu Lys Val Thr
             105                 110                 115

GGA TGC CCC AAG GAA GCT ACA GAG TCA ACT TTC AGG AAG TAC AGG GCA        440
Gly Cys Pro Lys Glu Ala Thr Glu Ser Thr Phe Arg Lys Tyr Arg Ala
         120                 125                 130

GAA GCT GTG TTG CTC TTC TCT CTG GTT GTT TTC TAC CTG ACA CTC ATC        488
Glu Ala Val Leu Leu Phe Ser Leu Val Val Phe Tyr Leu Thr Leu Ile
             135                 140                 145

ATT TTC ACC TGC AAA TTT GCA CGA CTA CAA AGC ATT TTC CCA GAT ATT        536
Ile Phe Thr Cys Lys Phe Ala Arg Leu Gln Ser Ile Phe Pro Asp Ile
     150                 155                 160

TCT AAA CCT GGT ACG GAA CAA GCT TTT CTT CCA GTC ACC TCC CCA AGC        584
Ser Lys Pro Gly Thr Glu Gln Ala Phe Leu Pro Val Thr Ser Pro Ser
165                 170                 175                 180

AAA CAT TTG GGG CCA GTG ACC CTT CCT AAG ACA GAA ACG GTA                626
Lys His Leu Gly Pro Val Thr Leu Pro Lys Thr Glu Thr Val
                 185                 190

TGAGTAGGAT CTCCACTGGT TTTTACAAAG CCAAGGGCAC ATCAGATCAG TGTGCCTGAA      686
TGCCACCCGG ACAAGAGAAG AATGAGCTCC ATCCTCAGAT GGCAACCTTT CGAAGTCCTT      746
CACCTGACAG TGGGCTCCAC ACTACTCCCT GACACAGGGT CTTGAGCACC ATCATATGAT      806
CACGAAGCAT GGAGTATCAC CGCTTCTCTG TGCTGTCAGC TTAATGTTTC ATGTGGCTAT      866
CTGGTCAACC TCGTGAGTGC TTTTCAGTCA TCTACAAGCT ATGGTGAGAT GCAGGTGAAG      926
CAGGGTCATG GGAAATTTGA ACACTCTGAG CTGGCCCTGT GACAGACTCC TGAGGACAGC      986
TGTCTCTCCT ACATCTGGGA TACATCTCTT TGAATTTGTC CTGTTTCGTT GCACCAGCCC     1046
AGATGTCTCA CATCTGGCGG AAAATTGACAG GCCAAGCTGT GAGCCAGTGG GAAATATTTA    1106
GCAAATAATT TCCAGTGGCG AAGGTCCTGC TATTAGTAAG GAGTATTATG TGTACATAGA     1166
AATGAGAGGT CAGTGAACTA TTCCCCAGCA GGGCCTTTTC ATCTGGAAAA GACATCCACA     1226
AAAGCAGCAA TACAGAGGGA TGCCAGCATT TATTTTTTA ATCTTCATGT ATTGTCAAAG      1286
AAGAATTTTT CATGTTTTTT CAAAGAAGTG TGTTTCTTTC CTTTTTAAA ATATGAAGGT     1346
```

```
CTAGTTACAT AGCATTGCTA CGTACAAGCA GCCTGAGAGA AGATGGAGAA TGTTCCTCAA   1406

AATAGGGACA GCAAGCTAGA ACGACTGTAC AGTGCCTGCT GGGAAGGGCA GACAATGGAC   1466

TGAGAAACCA GAAGTCTGGC CACAAGATTG TCTGTATGAT TCTGGACGAG TCACTTGTGG   1526

TTTTCACTCT CTGGTTAGTA AACCAGATAG TTTAGTCTGG GTTGAATACA ATGGATGTGA   1586

AGTTGCTTGG GGAAAGCTGA ATGTAGTGAA TACATTGGCA ACTCTACTGG GCTGTTACCT   1646

GTTGATATCC TAGAGTTCTG GAGCTGAGAC GATCGCTGTC ATATCTCAGC TTGCCCATCA   1706

ATCCAAACAC AGGAGGCTAC AAAAAGGACA TGAGCATGGT CTTCTGTGTG AACTCCTCCT   1766

GAGAAACGTG GAGACTGGCT CAGCGCTTTG TGCTCGAAGG ACTAATCACA AGTTCTTCGA   1826

AGATATGGAC CTAGGGGAGC TATTGCGCCA CGACAGGAGG AAGTTCTCAG ATGTTGCATT   1886

GATGTAACAT TGTTGCATTT CTTTAATGAG CTGGGCTCCT TCCTCATTTG CTTCCCAAAG   1946

AGATTTTGTC CCACTAATGG TGTGCCCATC ACCCACACTA TGAAAAGTAA AAGGGATGCT   2006

GAGCAGATAC AGGCTAGTCT TACCTCTCAA GTCCATGACT TTCATGCTAT TAAAGAATGC   2066

ATGTGAAGAG GTGTGTTCTT CTTTTCTATC TTTAAAATGA TCGACTTTAG AGTGAGTGTT   2126

TGGGTGCTGA GTGGAGAGTA AGAATGCAGA AATGGTAGTG GTAAATGACT GGCTGCTTCC   2186

CGAGGGGATC C                                                       2197
```

( 2 ) INFORMATION FOR SEQ ID NO:4:

( i ) SEQUENCE CHARACTERISTICS:
        ( A ) LENGTH: 194 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Gln Gly Leu Gln Leu Leu Phe Leu Gly Cys Ala Ala Trp His
 1               5                  10                  15

Arg Asp Gly Asp Val Glu Val Thr Val Ala Cys Ser Glu Thr Ala Asp
            20                  25                  30

Leu Pro Cys Thr Ala Pro Trp Asp Pro Gln Leu Ser Tyr Ala Val Ser
        35                  40                  45

Trp Ala Lys Val Ser Glu Ser Gly Thr Glu Ser Val Glu Leu Pro Glu
    50                  55                  60

Ser Lys Gln Asn Ser Ser Phe Glu Ala Pro Arg Arg Ala Tyr Ser
65                  70                  75                  80

Leu Thr Ile Gln Asn Thr Thr Ile Cys Ser Ser Gly Thr Tyr Arg Cys
                85                  90                  95

Ala Leu Gln Glu Leu Gly Gly Gln Arg Asn Leu Ser Gly Thr Val Val
            100                 105                 110

Leu Lys Val Thr Gly Cys Pro Lys Glu Ala Thr Glu Ser Thr Phe Arg
        115                 120                 125

Lys Tyr Arg Ala Glu Ala Val Leu Leu Phe Ser Leu Val Val Phe Tyr
    130                 135                 140

Leu Thr Leu Ile Ile Phe Thr Cys Lys Phe Ala Arg Leu Gln Ser Ile
145                 150                 155                 160

Phe Pro Asp Ile Ser Lys Pro Gly Thr Glu Gln Ala Phe Leu Pro Val
                165                 170                 175

Thr Ser Pro Ser Lys His Leu Gly Pro Val Thr Leu Pro Lys Thr Glu
            180                 185                 190

Thr Val
```

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

GCCATGTCGC AAGGCCTCCA GCTCC        25

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

ACACGGTCTC CTGGGTCAAG        20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:7:

ACCTAAGTGG CAAGGTGATC        20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

GACAGCACTA TCATCAGAAG        20

( 2 ) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CTGCAGCTCG GGCACCTACA GGTG 24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:10:

CTGCAGCTCG GGCACCTACA GGTG 24

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TGCACAGCGT AAAGA 15

(2) INFORMATION FOR SEQ ID NO:12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

ACTTTTAAGA AATACAGAGC GGAGATTGTC CT 32

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single

```
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:13:

GAAATACAGA GCGGAGATTG TCCT                                              2 4

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:14:

ACACTCATCA TTTTCACTTG T                                                 2 1

( 2 ) INFORMATION FOR SEQ ID NO:15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:15:

AGCTTTTCTT CCAGTCACCT CCCCAA                                            2 6
```

LYMPHOCYTE ACTIVATION ANTIGENS AND ANTIBODIES THERETO

RELATED APPLICATIONS

This application is a continuation of application Ser. No. 08/233,005, filed Apr. 25, 1994, now U.S. Pat. No. 5,710,262, issued Jan 20, 1998, which is a continuation-in-part of application Ser. No. 07/870,029, filed Apr. 17, 1992, now U.S. Pat. No. 5,316,920, issued May 31, 1994.

GOVERNMENT RIGHTS

Part of the work leading to this invention was made with United States Government funds. Therefore, the U.S. Government has certain rights in this invention.

FIELD OF THE INVENTION

This invention relates to nucleic acid sequences encoding human lymphocyte activation antigens, particularly to sequences encoding lymphocyte activation antigen HB15, and to the proteins and polypeptides encoded by those sequences.

BACKGROUND OF THE INVENTION

The Ig gene superfamily, described by Williams et al., Annu. Rev. Immunol., 88:381–405 (1988), encompasses a large family of genes that are presumed to have evolved from a common precursor. Many of the Ig superfamily members are involved in cell-cell adhesion and signal transduction. In addition, many of the cell-surface molecules which regulate immune responses contain conserved structural features similar to those found in immunoglobulin (Ig). While most members of the Ig gene superfamily contain multiple linearly-assembled Ig-like domains, several proteins have been identified that contain single Ig-like domains.

Single Ig-like domain proteins that are known or assumed to be involved in cell-cell adhesion include: CD8α (Littman et al., Cell 40:237 (1985)), CD8β (Johnson et al., Nature 323:74 (1986)), CD7 (Aruffo et al., EMBO J. 6:3313 (1987)), Thy-1 (Williams et al., Science 216:696 (1982)), CD28 (Aruffo et al., Proc. Natl. Acad. Sci. USA 84:8573 (1987)), CTLA-4 (Brunet et al., Nature 328:267 (1987)) and Po which is a structural protein of the peripheral myelin sheath (Lemke et al., Cell 40:501 (1985)). In addition, other single Ig-domain containing proteins associate with the antigen receptors of B and T lymphocytes, forming multimeric signal-transducing complexes. These include: CD3 γ, δ and ε chains (Gold et al., Nature 321:431–434 (1986); van den Elsen et al., Nature 312:413–418 (1984)), CD79β (Hermanson et al., Proc. Natl. Acad. Sci., USA 85:6890 (1988)), and CD79α (Sakaguchi et al., EMBO J. 7:3457–3464 (1988)).

Two proteins containing single Ig-like domains found on lymphocytes are preferentially associated with cellular activation and are known to be involved in mediating cell-cell interactions. CD28 is expressed much more on activated than nonactivated T and B lymphocytes (Turka et al., J. Immunol. 144:1646 (1990)), and CTLA-4 is expressed mostly, if not exclusively, by activated T and B lymphocytes (Brunet et al., Nature 328:267 (1987); Harper et al., J. Immunol. 147:1037–1044 (1991)). The role of CD28 as a T cell receptor for the CD80 molecule expressed by activated B cells has been recently identified (Linsley et al., Proc. Natl. Acad. Sci. USA 87:5031–503 (1990); Freeman et al., J. Immunol. 143:2714–2722 (1989)), as has a similar role for CTLA-4 (Linsley et al., J. Exp. Med. 174:561–569 (1991)). As with CD28 and CD80, most of the Ig-like domain-containing receptors interact with members of the Ig superfamily present on other cells.

It is an object of the invention to provide a new member of the Ig gene superfamily. Another object of the invention is to provide a protein that is found predominantly on lymphoid tissue. Yet another object of the invention is to provide a protein that contains an extracellular single Ig-like domain. Yet another object of the invention is to provide a nucleic acid encoding the protein or a biologically active portion of the protein. Another object of the invention is to provide nucleic acid probes for identifying the protein or homologs thereof. Yet another object of the invention is to provide an antigen that is present on activated lymphocytes, but absent on inactive lymphocytes and most other cell types.

SUMMARY OF THE INVENTION

The invention is based on the discovery of a human lymphocyte cDNA which encodes a novel glycoprotein present on activated lymphocytes, termed HB15 or CD83 (WHO nomenclature).

The invention thus features a nucleic acid isolate encoding the polypeptide HB15 and able to hybridize to a nucleic acid encoding a polypeptide having an amino acid sequence shown in SEQ ID NO:2. HB15 mammalian analog refers to a polypeptide which has a tissue distribution similar to human HB15, i.e., is present on activated lymphocytes and dendritic cells, and is encoded by a nucleic acid able to hybridize to a nucleic acid encoding the amino acid sequence shown in SEQ ID NO:2. "HB15 fragment" or "HB15 analog fragment" refers to a polypeptide of at least 5 amino acids, preferably at least 10 amino acids, and most preferably at least 20 amino acids, which in its native context is part of a protein having the tissue distribution pattern of HB15. An HB15 fragment or HB15 analog fragment will include a portion of HB15 such as one of the extracellular, transmembrane or cytoplasmic domains, or a smaller polypeptide, such as an immunogenic region of HB15.

In preferred embodiments, the nucleic acid isolate encodes a polypeptide that is recognized by a monoclonal antibody specific for an HB15 epitope. Preferably, the nucleic acid isolate encodes a polypeptide having the complete amino acid sequence shown in SEQ ID NO:2, or the portion of SEQ ID NO:2 comprising the HB15 extracellular domain (i.e., amino acid numbers 1–125), the transmembrane domain (i.e., amino acid numbers 126–147), or the cytoplasmic domain (i.e., amino acid numbers 148–186). The boundaries of the mouse domains are approximately the same as those of the human domains, provided the sequences are aligned as shown in FIG. 6. Preferably, for polynucleotides greater than about 50 bases, the nucleic acid isolate is hybridizable under stringent conditions to a portion of the nucleic acid sequence of SEQ ID NO: 1. For oligonucleotides less than about 50 nucleotides in length, the nucleic acid isolate is hybridizable under low stringency conditions, i.e., at about 42° C. in the presence of 30% formamide according to conditions described in Benton and Davis (1977, Science 196:180), hereby incorporated by reference. Preferably, the nucleic acid isolate is greater than about 15 nucleotides, more preferably greater than about 20, 50 or 100 nucleotides.

The invention also encompasses replicable expression vectors containing nucleic acid sequences encoding the HB15 protein or portions thereof, including an HB15 domain, as defined above, or immunogenic fragments, and host cells transfected with such a vector (e.g., for a bacterial, yeast, or eucaryotic cell culture).

The invention also encompasses HB15 or portions thereof which are immunogenic, and thus useful as immunogens in order to raise antibodies against HB15 or portions thereof including any of its specific domains or fragments thereof.

The invention also features antibodies reactive with HB15 or fragments thereof.

The invention also features methods of producing human HB15 or a mammalian homolog of human HB15, comprising transforming a host cell with a nucleic acid encoding a polypeptide able to hybridize to a sequence encoding the amino acid sequence shown in SEQ ID NO: 2, culturing the transformed cell, and recovering the HB15 protein or homolog from the cell culture.

The invention also encompasses methods of detecting the presence of human HB15 or of a mammalian HB15 analog on a cell, comprising subjecting a cell suspected of bearing HB15 on its surface to an antibody that recognizes HB15, and detecting binding of the antibody to the cell.

The invention also features methods of producing a polypeptide encoded by a nucleic acid isolate greater than about 15 bp and capable of hybridizing under low or high stringency conditions to a nucleic acid sequence shown in SEQ ID NO: 1. The method includes the steps of (a) providing cells which in the untransfected form do not express a nucleic acid isolate greater than about 15 bp and hybridizable to a nucleic acid sequence shown in SEQ ID NO: 1; (b) transfecting the cells with the nucleic acid isolate operably linked to suitable control sequences under conditions effective for the production of the encoded polypeptide; and (c) recovering the polypeptide.

The invention thus also features a polypeptide having HB15 biological activity and encoded by a nucleic acid isolate able to hybridize under low or high stringency conditions to a nucleic acid encoding a polypeptide having the amino acid sequence shown in SEQ ID NO: 2. In addition, the invention includes a polypeptide encoded by a nucleic acid isolate greater than about 15 nucleotides, hybridizable under low or high stringency conditions to the complement of the nucleic acid sequence shown in SEQ ID NO: 1.

The invention also features a purified nucleic acid molecule encoding an amino acid sequence of an HB15 molecule from an animal species other than human, the nucleic acid molecule being isolated by: (1) hybridizing a nucleic acid isolate with a population of nucleic acid molecules from an animal species other than human, preferably under low stringency hybridization conditions, wherein the nucleic acid isolate encodes HB15 or a portion thereof that is recognizable by a monoclonal antibody specific for an HB15 determinant, and is able to hybridize under stringent conditions to a nucleic acid encoding a polypeptide having the amino acid sequence shown in SEQ ID NO: 2 ; (2) identifying a first nucleic acid molecule to which the nucleic acid isolate stringently hybridizes; and (3) isolating the first nucleic acid molecule, wherein the first nucleic acid molecule encodes a polypeptide having an amino-acid sequence shown in SEQ ID NO. 2.

This purified nucleic acid molecule may be further isolated by the additional steps of: (4) hybridizing a nucleic acid isolate with a population of nucleic acid molecules from an animal species other than human wherein said nucleic acid isolate encodes HB15 or is recognizable by a monoclonal antibody specific for an HB15 determinant, and is able to hybridize to a nucleic acid encoding a polypeptide having the amino acid sequence shown in SEQ ID NO: 2; (5) identifying a second nucleic acid molecule to which the nucleic acid isolate hybridizes; and (6) isolating the second nucleic acid, wherein the first and second nucleic acid molecules, joined together in an amino acid reading frame, encode an amino acid sequence of SEQ ID NO. 2.

Preferably, the nucleic acid molecule is a murine nucleic acid.

The invention also features an isolated nucleic acid able to hybridize to the nucleic acid molecule described immediately above, and polypeptides encoded by that nucleic acid molecule.

As used herein the term "identify" is intended to include techniques that require detection, isolation or purification of HB15 protein or its encoding genetic material. The terms "isolated" and "essentially purified" refer to a nucleic acid or protein sequence that has been separated or isolated from the environment in which it was prepared or in which it naturally occurs.

Nucleic acid or protein sequences may be in the form of chimeric molecules, i.e., which lack one or more of the three domains found in the native molecule, or chimeric hybrids in which one domain is substituted with a domain from another type of molecule, e.g., a toxin or an Ig molecule. Examples of chimeric hybrids include but are not limited to molecules which contain extracellular domains in which one or more of these domains are heterologous. Such hybrids, e.g., an immunoglobulin fusion protein, are useful for promoting serum half-life or multimerization of the molecule to increase avidity. Truncated HB15 molecules include but are not limited to HB15 comprising an extracellular domain free of transmembrane and cytoplasmic domains, which is useful for identifying a ligand or disrupting cell/cell interaction, e.g., dendritic/T cell interactions.

The term "immunogenic fragment" refers to a fragment of HB15 that reacts with antibodies specific for a determinant of HB15.

The HB15 protein or immunogenic fragment can be used as antigenic reagents for immunization of a host animal in the preparation of antibodies specific for HB15. An HB15 antibody may also be used to deliver drugs, toxins, or imaging agents to cells that express HB15. HB15 cDNA can be used to produce these proteins or peptide fragments; to identify nucleic acid molecules encoding related proteins or polypeptides (e.g., homologous polypeptides from related animal species and heterologous molecules from the same species); or to construct genes encoding other new, chimeric molecules. In addition, HB15 cDNA can be used to synthesize antisense oligonucleotides for inhibiting the expression of the HB15 protein. Assays for HB15 production or expression by cells are made possible by the development of monoclonal antibodies selectively reactive with the HB15 protein.

Other features and advantages of the invention will be apparent from the following description of the preferred embodiments thereof and from the claims.

BRIEF DESCRIPTION OF THE DRAWINGS

FIG. 2 shows the cDNA nucleotide sequence (SEQ ID NO:1) and the deduced amino acid sequence (SEQ ID NO:2) of HB15; the vertical arrow represents the predicted cleavage site for generation of the mature protein; numbers shown above the amino acid sequence designate amino acid residue positions of the putative mature protein; numbers to the right of the nucleotide sequence designate nucleotide positions; the * indicates the translation termination codon; underlined nucleotides delineate translated regions with hydrophobic character; underlined amino acids indicate potential N-linked glycosylation attachments sites; wavy underlining delineates a poly (A) attachment signal sequence; amino acids conserved in Ig-like domains are indicated by (+); cysteine residues are circled; arrowheads below the nucleotide sequence denote exon/intron boundaries;

FIG. 6 is a comparison of human and mouse CDNA sequences encoding HB15.

FIG. 7 presents sequence locations of oligonucleotide probes used for PCR amplification of human and mouse HB15 cDNAs relative to the human and mouse HB15 DNA sequences.

DESCRIPTION OF THE PREFERRED EMBODIMENTS

Figure 1:
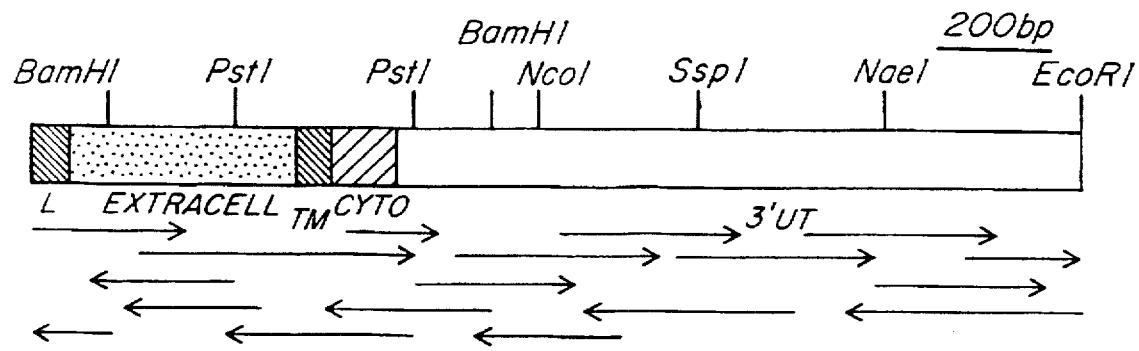
FIG. 1 shows the structure of the HB15 cDNA clone and the location of restriction sites, showing the extracellular domain ("extracell"), the transmembrane domain ("TM"), and the 3' untranslated region (3'UT)

The lymphocyte activation antigen, HB15, is expressed virtually exclusively by lymphoid tissue and skin Langerhans cells. HB15 is a single-chain cell-surface glycoprotein of $M_r$ 45,000. Referring to FIG. 1, the structural features of the HB15 protein, predicted from nucleotide sequence derived from multiple cDNA clones, establish it as a new member of the Ig superfamily. The predicted structure of HB15 is that of a typical membrane glycoprotein with a single extracellular Ig-like domain, a transmembrane domain and an approximately 40 amino acid cytoplasmic domain. cDNA cloned from a human lymphocyte library were analyzed and shown to encode the novel cell-surface glycoprotein HB15, expressed by activated lymphocytes. The mature 186 amino acid protein encoded by the cDNA was composed of a single extracellular V type immunoglobulin (Ig)-like domain, a transmembrane domain and a 39 amino acid cytoplasmic domain. Northern blot analysis revealed that HB15 derives from three mRNA transcripts of ~1.7, 2.0 and 2.5 kb expressed by lymphoblastoid cell lines. It is likely that the entire coding region for HB15 was identified, as transfection of cell lines with the pHB15 cDNA generated cell surface expression of the protein and the $M_r$ of the immunoprecipitated protein was similar in both cDNA transfected cells (~45,000) and HB15⁺ Raji cells (~40,000). It is also likely that HB15 undergoes extensive post-translational processing, as HB15 was expressed as a single chain molecule, yet the determined $M_r$ was twice the predicted size of the core protein. Since HB15 was also expressed on the surface of cDNA transfected cells, including COS cells, CHO cells, a mouse pre-B cell line and a human erythroleukemia line, it is likely that surface expression is not dependent on expression of other components of a molecular complex as occurs with the Ig-like proteins that associate with the T and B cell antigen receptors.

Monoclonal antibodies reactive with HB15 were produced and used to show that HB15 expression is specific for lymphoblastoid cell lines and mitogen-activated lymphocytes; HB15 was not expressed at detectable levels by circulating leukocytes. Immunohistological analysis revealed that HB15 has a unique pattern of expression among tissues, being found predominantly in hematopoietic tissues with scattered expression by interfollicular cells and weak expression by mantle zone and germinal center cells. Uniquely, HB15 is also expressed by Langerhans cells within the skin and circulating dendritic cells. Thus, the HB15 glycoprotein represents a new member of the Ig superfamily.

Comparison of the HB15 amino acid sequences (SEQ ID NO:2) with other previously identified proteins did not reveal any striking homologies, except the similarity of the extracellular Ig-like domain with other members of the Ig superfamily. The HB15 Ig-like domain contained many of the conserved features found in the V-set of domains, as shown in FIG. 2 (Williams et al., Ann. Rev. Immunol. 88:381–405 (1988)). Based on the homology with Ig domains, HB15 is likely to possess a disulfide bond linking Cys 16 and Cys 88. This would place 71 amino acids between the two Cys residues which is of the appropriate size for V-related domains (Williams et al., supra). There is the potential for additional disulfide bond formation between residues at positions 8, 81 and 110 since these Cys are present in the extracellular domain as well. In addition, HB15 has a Cys residue located within the predicted membrane spanning domain at position 144. Cys residues are also located at identical positions in CD3δ and CD7, suggesting some functional significance, perhaps as sites for fatty acylation (Kaufman et al., J. Biol. Chem. 259:7230–7238, (1984); Rose et al., Proc. Natl. Acad. Sci., USA 81:2050–2054 (1984)). The HB15 cytoplasmic tail is similar in size to that of CD7 (Aruffo et al., EMBO J. 6:3313 (1987)), but shared no amino acid sequence similarity with known proteins. However, the five Ser/Thr residues within this domain could serve as potential sites of phosphorylation. Thus, HB15 appears to be a newly described lymphocyte cell surface antigen that shares no apparent relatedness with previously described structures.

The HB15 extracellular domain is different from the typical Ig-like domain in that it is encoded by at least two exons. Analysis of partial genomic DNA sequence revealed that half of the Ig-like domain is encoded by a single exon and the putative membrane spanning domain is also encoded by a distinct exon (FIG. 2). That Ig-like domains can be encoded by more than one exon has been observed for some members of the Ig superfamily, including the Po protein (Lemke et al., Neuron 1:73–83 (1988)), CD4 (Littman et al., Nature 325:453–455 (1987)) and N-CAM (Owens et al., Proc. Natl. Acad. Sci., USA 84:294–298 (1987)). This finding supports structural analyses which suggested that Ig domains may have arisen from an ancestral half-domain that evolved through duplication and subsequent adjoining. However, each of the above genes and the HB15 gene contain introns at different locations between the sequences coding for the conserved Cys residues of the disulfide bond (Williams et al., Annu. Rev. Immunol. 88:381–405 (1988)). This finding supports the notion that introns may have been subsequently inserted to interrupt the ancestral Ig-like domain at later points during the evolution of each of these domains.

Expression of HB15 appears to be generally restricted to lymphocytes since two monoclonal antibodies reactive with HB15 failed to detect HB15 on most other hematopoietic cells. HB15 expression may be a late event in lymphocyte development as most thymocytes and circulating lymphocytes did not express detectable levels of cell surface HB15. However, after being activated by mitogens, peripheral lymphocytes expressed maximal levels of cell surface HB15 on days 3 through 5, the period of time during which maximal proliferation occurred. HB15 may be expressed at low levels by monocytes, especially after culture or activation, but the level of expression is low and may just result from Fc receptor mediated antibody attachment. Many T exd B cell lines also expressed HB15, but expression was generally at low levels. Interestingly, cell-surface HB15 expression by cell lines was highest during periods of maximal proliferation such as on the first day after the cultures were fed. These results imply that HB15 is important for maximal growth of lymphoblastoid cells or the maximal growth of cells is critical for the expression of this antigen. This was consistent with the observation that HB15 was expressed by germinal center cells in hematopoietic tissues. Nevertheless, HB15 expression appeared to be lymphoid tissue restricted as revealed by immunohistological analysis of twenty-two different tissues. The only exception was the finding that skin Langerhans cells express HB15. This unique pattern of restricted expression, along with the structural analysis of the protein, indicates that HB15 is a newly identified lymphocyte activation antigen.

The structural similarity of HB15 with other members of the Ig superfamily suggests that it may be involved in cellular interactions, since Ig-like domains are frequently involved in a variety of homotypic and heterotypic interactions in the immune and nervous systems. These interactions include binding functions that trigger a subsequent event below the cell surface or adhesion. A key functional feature is that homophilic or heterophilic binding usually occurs between Ig-related molecules, and this is often between molecules on opposed membrane surfaces. The structural relatedness of HB15 to these other proteins may imply a role for this lymphocyte activation protein in either homotypic or heterotypic interactions of lymphocytes following activation of other HB15$^+$ cell types. As used herein, "homophilic" refers to cells of the same type that have a specific association or attraction for each other; "homotypic" refers to two molecules or cells of the same form that interact in a specific fashion; "heterophilic" refers to cells of different types having a specific association with each other; and "heterotypic" refers to two molecules or cells of different types that interact in a specific fashion.

It is understood that the particular nucleotide (SEQ ID NO:1) and amino acid (SEQ ID NO:3) sequences disclosed in FIG. 2 are representative of the human counterpart, and that related mammalian genes and their encoded proteins can be obtained following the teachings of this disclosure, as demonstrated herein for isolation of the mouse HB15 homolog. A mammalian homolog of the sequences disclosed in FIG. 2 will include a gene which is identified under stringent hybridizations conditions using a probe based on an approximately 20 nucleotide region of sequence identity between the FIG. 2 nucleotide sequence and the gene encoding the mammalian homolog. For example, cross-hybridization of the disclosed nucleic acid sequences with genetic material from human cells, can readily be performed to obtain equivalent human sequences; for example, see the oligonucleotide sequences presented in Table 1. In an analogous manner, degenerate oligonucleotides can readily be synthesized from the disclosed amino acid sequence, or portions thereof, and amplified using any well-known amplification technique, such as the polymerase chain reaction, to obtain probes that bind to equivalent human sequences. Proteins or polypeptides encoded by equivalent sequences can be produced. Antibodies directed against the disclosed protein or peptides can also be raised and employed to cross-react with human and other mammalian peptides having similar epitope(s). Those peptides isolated in this manner that have similar antibody reactivity patterns to those of the disclosed proteins or peptides are considered equivalents of the disclosed proteins or peptides.

The following examples are presented to illustrate the advantages of the present invention and to assist one of ordinary skill in making and using the same. These examples are not intended in any way otherwise to limit the scope of the disclosure.

EXAMPLE I

Human cDNA clones encoding HB15 were isolated and the encoded human HB15 protein characterized, as follows.

A human tonsil cDNA library was screened by differential hybridization (see Tedder et al., Proc. Natl. Acad. Sci., USA 85:208, 1988) , hereby incorporated by reference using labeled cDNA from the B lymphoblastoid cell line Raji and the T cell line H-SB2. Two of the 261 RAJI$^+$ H-SB2$^-$ cDNA clones isolated, pB10 (~2.5 kb) and pB123 (~1.2 kb), cross hybridized, yet failed to hybridize with cDNA that encode known B cell surface antigens (Tedder et al., supra).

Expression of the mRNA was examined by Northern blot analysis using poly(A)$^+$ RNA isolated from B cell lines (NALM-6, Namalwa, Daudi, SB, and Raji), T cell lines (Hut-78, H-SB2, and MOLT-3) and the erythroleukemia line, K562. Poly(A)$^+$ RNA was isolated as described (Maniatis et al., Molecular Cloning: A Laboratory Manual, (1982)). For Northern-blot analysis, 2 μAg of poly(A)$^+$ RNA was denatured with glyoxal, fractionated by electrophoresis through a 1.1% agarose gel and transferred to nitrocellulose (Thomas, Methods Enzymol. 100:255 (1983)). The pB123 CDNA insert used as probe was isolated, nick-translated (Rigby et al., J. Mol. Biol. 113:237–251 (1977)) and hybridized with the filters as described (Wahl et al., Proc. Natl.

Acad. Sci., USA 76:3683–3687 (1979)). Hybridization at high stringency was with 50% (v/v) formamide, 4×SSC, 10% (w/v) Na dextran sulfate at 42° C. The filters were washed at 65° C. with 0.2×SSC, 0.1% SDS. RNA size was determined by comparison with 28S and 18S ribosomal RNA run on the same gels as standards. The same blot was also hybridized with CDNA clones containing a housekeeping mRNA of unknown identity revealing that all mRNA were intact and were similar in quantity of this expressed mRNA. For hybridization at low stringency the conditions are overnight incubation at 42° C. in a solution comprising: 20% formamide, 5×SSC (150 mM NaCl, 15 mM trisodium citrate), 50 mM sodium phosphate (pH 7.6), 5×Denhardts solution, 10% dextran sulfate, and 20 μg/ml denatured, sheared salmon sperm DNA.

The pB123 cDNA hybridized strongly with three mRNA species of ~1.7, ~2.0 and ~2.5 kb in SB and Raji. Daudi and Namalwa cells expressed lower levels of this mRNA. Further autoradiography of the blot (7 days) revealed that the NALM-6, Hut-78 and MOLT-3 cells also expressed these three mRNA species, but at much lower levels, and faint hybridization with H-SB2 RNA was detected. These results suggested differential expression of this gene among leukocyte subpopulations.

Restriction maps were generated for these cDNA, as described by Maniatis et al., Molecular Cloning: A Laboratory Manual, 1982, Cold Spring Harbor Press, CSH, N.Y., and their nucleotide sequences determined as described Sanger et al., Proc. Nat. Aca. Sci. 74:5463, 1977. Both cDNA were overlapping and contained open reading frames at their 5' ends with the pB123 cDNA having the longest 5' sequence. Since neither clone contained a translation initiation site, the pB10 cDNA insert was used to isolate 13 additional cross-hybridizing cDNA from a human tonsil library. The pB10 insert was purified, labeled by nick translation (Rigby et al., J. Mol. Biol. 113:237–251 (1977)) and used to isolate homologous cDNA by again screening the same human tonsil cDNA library in λgt11 (Weis et al., Proc. Natl. Acad. Sci., USA 83:5639–5643 (1986)) as described (Zhou et al., Immunogenetics 35:102–111 (1992)). Positive plaques were isolated, cloned and the CDNA inserts were removed by EcoR I digestion and subcloned into pSP65 (Melton et al., Nucleic Acids Res. 12:7035–7056 (1984)). Restriction maps and nucleotide sequence determination indicated that 12 of the cDNA were overlapping, with one cDNA having the longest sequence at the 5' end. The restriction map and nucleotide sequence of this clone, termed pHB15, is shown in FIG. 1. The full length cDNA clone is likely to include an ~500 bp fragment at the 3' end that was removed from the CDNA by EcoR I digestion and subcloning. Eight other independent CDNA clones had similar EcoR I generated fragments and an EcoR I site was located at the identical nucleotide position in all cDNA that were sequenced.

The pHB15 cDNA had a 625 bp open reading frame, with the major portion of the cDNA representing untranslated sequence. The determined nucleotide sequence (SEQ ID NO:1) and predicted amino acid sequence (SEQ ID NO:2) of HB15 are given in FIG. 2. The predicted cleavage site used to generate the mature protein is shown by a vertical arrow. The numbers shown above the amino acid sequence designate amino acid residue positions of the putative mature protein and the numbers on the right designate nucleotide positions. Amino acids are designated by the single-letter code, and * indicates the termination codon. Nucleotides delineating translated regions with hydrophobic character are underlined. Amino acids indicating potential N-linked glycosylation attachment sites are underlined. A poly(A) attachment signal sequence is indicated by wavy underlining. The Cys residues are circled and amino acids which are often conserved in Ig-like domains are indicated by (+). Arrow heads below the nucleotide sequence denote exon/intron boundaries identified in another DNA clone.

The first ATG shown is the most likely initiation codon for translation since it conforms to the proposed translation initiation consensus sequence, (A/G)CCAUG (Kozak, Cell 44:283–292 (1986)). It is likely that the different mRNA species result from differential use of poly(A) attachment sites, AATAAA, since one was found at nucleotide position 1248 in the middle of the 3' untranslated region (FIG. 2). This poly(A) attachment site was functional in the pB123 CDNA since it was followed by a poly(A) tail. A poly(A) attachment site or tail was not found in the ~550 bp EcoR I fragment which presumably represents the 3' end of the pHB15 cDNA.

One clone isolated from the cDNA library (~3.0 kb long) that hybridized with the pB123 cDNA had a unique sequence with 229 and 107 bp long segments that were identical to those found in the other cDNA. These regions had flanking sequences that corresponded to the consensus 5' and 3' splice sequences which demark exon boundaries (Aebi et al., Trends Genet. 3:102–107 (1987)) indicating that this aberrant CDNA was composed of introns and two exons. The three splice junction sites identified by this clone are shown (FIG. 2).

The predicted length of the HB15 protein was 205 amino acids (FIG. 2). However, the pB123 cDNA was missing the codon AAG at nucleotide position 500 so the protein may be one amino acid shorter in some cases. This may result from differential splicing at an exon/intron border, that results in the inclusion or loss of a codon since this codon abuts a potential splice site. A similar phenomenon has been found in the CD19 gene which also encodes a member of the Ig superfamily (Zhou et al., Immunogenetics 35:102–111 (1992)). Hydropathy analysis of the HB15 amino acid sequence by the method of Kyte et al., J. Mol. Biol. 157:105 (1982) revealed two regions of strong hydrophobicity. The first hydrophobic stretch of 19 amino acids represents a typical signal peptide at the amino terminal end of the protein. The algorithm of von Heijne, Nucleic Acids Res. 14:4683–4690 (1986) predicts that the most probable aminoterminus of the mature protein would be the Thr following amino acid 19. The second hydrophobic region of 22 amino acids most probably represents the transmembrane region. Three potential N-linked glycosylation attachment sites (N-X-S/T) were found in the extracellular domain. Therefore, the predicted molecular mass of the core protein would be ~20,500.

Six Cys residues were found in the extracellular domain of HB15 and one in the putative membrane spanning domain. One pair of these residues at positions 16 and 88 delineate Ig-like domains (Williams et al., Annu. Rev. Immunol. 88:381–405 (1988)). This domain contained many of the hallmark amino acids which define the V set of Ig-like domains. A computer search of nucleotide and protein sequences was conducted using the Protein Identification Resource Data (GenBank release 66 and Swiss-Prot-16). Gap penalties of −1 were assessed during sequence homology analysis for each nucleotide or amino acid in the sequence where a gap or deletion occurred. The computer search of protein sequences showed that no proteins shared significant sequence homology with HB15 other than some members of the Ig superfamily.

Figure 3:
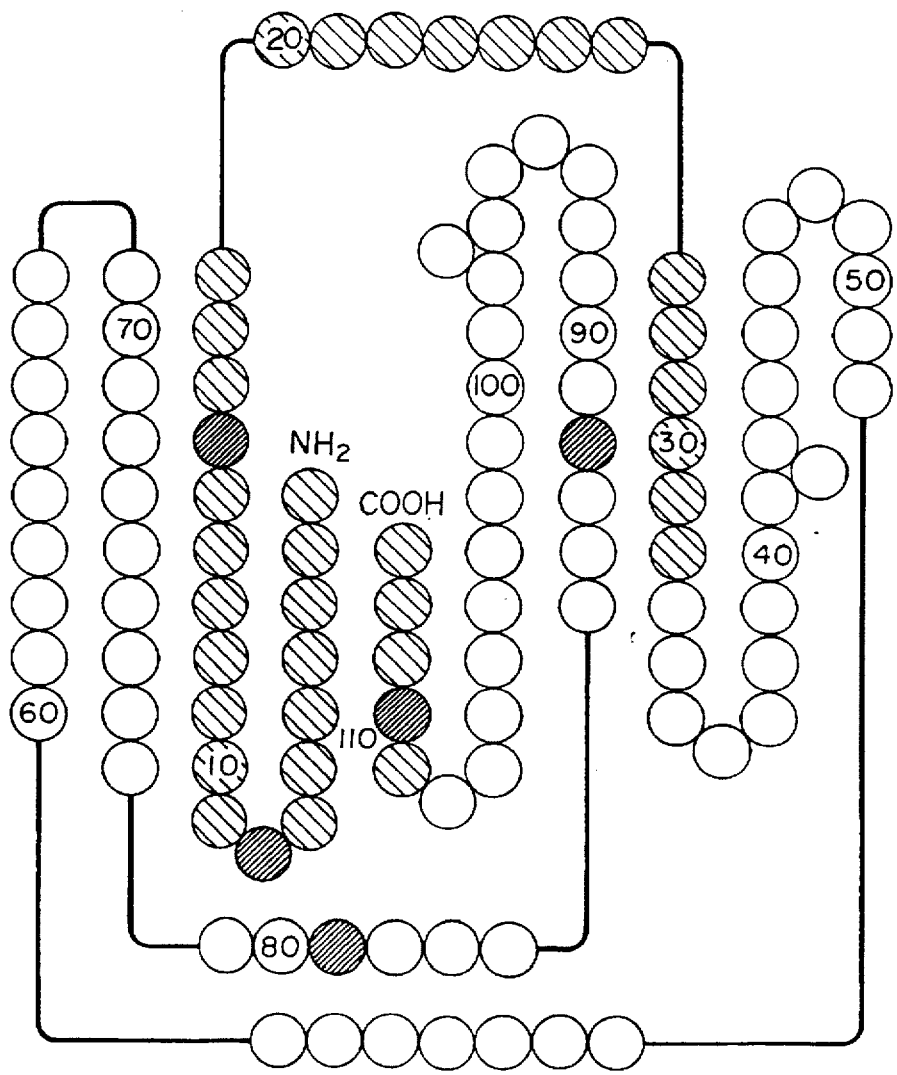
FIG. 3 shows a hypothetical model for the structure of the extracellular domain of HB15, cysteine residues are shown as filled in circles; amino acids encoded by different exons are indicated by alternatively shaded circles; numbers represent the predicted amino acid residue positions as shown in FIG. 2.

Referring to FIG. 3, a hypothetical model is given for the structure of the extracellular domain of HB15 based on the proposed arrangement of the β-pleated sheets for the V domain of Ig heavy chain. Cys residues are represented as filled circles and amino acids encoded by different exons are indicated by alternatively shaded circles. Numbers represent the predicted amino acid residue positions as in FIG. 2.

EXAMPLE II

Preparation of HB15 Truncated and Chimeric Molecules

Variant forms of HB15, e.g., truncated molecules or chimeric (i.e., hybrid) molecules containing substituted domains, may be prepared using conventional recombinant DNA techniques known to those of skill in the art and the HB15 nucleotide sequences (SEQ ID NO:1—human and SEQ ID NO:3—mouse and amino acid sequences (SEQ ID NO:2—human and SEQ ID NO:4—mouse) disclosed herein. See Maniatis et al., 1982, Molecular Cloning, Cold Spring Harbor Laboratory, Cold Spring Harbor, N.Y., hereby incorporated by reference.

A chimeric HB15 molecule is one in which one or two of the extracellular, transmembrane, and cytoplasmic domains is removed and replaced by the corresponding domain from another species, e.g., a domain from the mouse sequences disclosed herein.

A truncated HB15 molecule is one in which a portion of the molecule has been deleted. Truncated molecules will include those molecules in which one or both of the transmembrane and cytoplasmic domains has been deleted from the molecule, leaving, minimally, the extracellular domain or a portion thereof. A truncated HB15 molecule may be used to construct a protein in which the truncated HB15 end is fused to an effector molecule such as a drug toxin, or imaging agent using conventional methods for joining such molecules at the DNA or polypeptide level.

For example, a truncated form of HB15 may include the extracellular domain free of the cytoplasmic and transmembrane domains. This representative truncated HB15 molecule may be constructed by cleaving a DNA fragment containing a nucleotide sequence encoding the extracellular domain using standard PCR amplification to amplify that region. The amplified fragment then may be ligated to compatible ends of an expression vector and transfected into a host cell, e.g., an activated lymphocyte, which allows for production of the encoded domain. Truncated molecules containing other portions of the HB15 molecule may be constructed using conventional PCR amplification procedures. One or more of these sites may be utilized, depending upon which domains of the HB15 molecule are preferred.

Chimeric forms of HB15 also may be constructed using conventional recombinant DNA technology and the nucleotide (SEQ ID NO:1—human and SEQ ID NO:3—mouse) and amino acid sequences (SEQ ID NO:2—human and SEQ ID NO:4—mouse) disclosed herein. For example, where a chimeric molecule comprising human extracellular and transmembrane HB15 domains and a murine cytoplasmic domain is desired, the human domains may be isolated using restriction enzymes which generate those portions of human HB15 and joined to a murine cytoplasmic domain using cloning techniques, and expressed as described above for truncated molecules.

EXAMPLE III

Isolation of Mammalian Homolog of HB15

A nucleotide sequence encoding HB15 from another mammalian species may be isolated by first hybridizing a nucleic acid probe with a population of nucleic acid molecules from an animal species other than human under hybridization conditions sufficient to allow for annealing of the probe to a homologous region of the target gene.. The nucleic acid probe may encode full-length human HB15 or a fragment thereof; the encoded polypeptide will be recognizable by a monoclonal antibody specific for an HB15 determinant, and will be able to hybridize to a nucleic acid encoding a polypeptide having the amino acid sequence shown in SEQ ID NO: 2. The probe will thus identify a first nucleic acid molecule to which the probe preferably stringently hybridizes. The first nucleic acid molecule then may be isolated and will thus encode a polypeptide having an amino acid sequence shown in SEQ ID NO. 2.

If a partial HB15 molecule, e.g., a heterologous domain is isolated in lieu of an entire HB15 molecule, a second nucleic acid molecule to which the nucleic acid probe preferably stringently hybridizes may be identified and isolated, wherein the first and second nucleic acid molecules, joined together in an amino acid reading frame, encode an amino acid sequence of SEQ ID NO. 2.

Alternative strategies may also be used for isolating a mammalian HB15 homolog. For example, the mouse HB15 homolog was isolated as follows.

The mouse HB15 gene was isolated by screening a murine genomic library by cross-hybridization with a 1.7 kb subclone of the human HB15 CDNA under low stringency conditions.

Genomic DNA clones were isolated from a genomic DNA library made with partial Mbo I-digested mouse genomic DNA that was isolated from a 129Sv mouse strain and inserted into the vector lambda-DASH II (Stratagene, La Jolla, Calif.). The human HB15 cDNA clone was labeled by nick translation and used to screen the mouse genomic DNA library according to the method of Benton and Davis (1977, Science 196:180). Hybridization was performed at 42° C. in the presence of 30% formamide and the filters were finally washed at 50° C. in 1×SSC with 0.1% SDS (w/v). The human HB15 cDNA probe contained the entire protein coding sequence and the entire 3' untranslated regions. Positive plaques were isolated, and phage DNA were characterized by restriction enzyme mapping as described (Maniatis et al., 1982, Molecular Cloning, supra). DNA fragments of these clones were generated by EcoR I or Hind III digestions and were subcloned into the plasmids pSP65 or pSP64. Detailed restriction enzyme maps of the subclones were made. Exons were located by Southern hybridization analysis of endonuclease digested mouse genomic DNA clones using labeled human cDNA or oligonucleotide probes. Nucleotide sequences were determined by the dideoxy chain termination method (Sanger et al., 1977, Proc. Nat. Aca. Sci. 74:5463).

Overlapping mouse genomic clones spanning 23 kb contained most of the mouse HB15 gene, from the 3' half of the immunoglobulin domain through the 3' untranslated region. Sequence analysis of the 3' portion of the immunoglobulin-like domain, the transmembrane region, and the cytoplasmic domain demonstrated a significant degree of conservation between human and mouse sequences, such that amino acid identity is ~70% in these exons (FIG. 6). Likewise, the 3' untranslated region contained 1600 bp of extremely well conserved nucleotide sequence.

FIG. 6 shows the nucleotide sequence of mouse HB15 (m) (SEQ ID NO:3) compared with the human (h) cDNA sequence (SEQ ID NO:1). The precise nucleotide sequence for the 5' region of the mouse HB15 protein is not definitive as indicated by nucleotides in lower case print. "*" indicates identity in nucleotide sequences between human and mouse. "–" indicates gaps in the nucleotide sequence introduced to generate the highest levels of homology. The predicted cleavage site used to generate the mature protein is shown by a vertical arrow. The numbers shown above the amino acid sequence designate amino acid residue positions of the mature human protein and the numbers on the right designate nucleotide positions for the human cDNA. Nucleotides delineating translated regions with hydrophobic character (leader and transmembrane domains) are double underlined. Amino acids indicating potential N-linked glycosylation attachment sites are underlined. A poly(A) attachment signal sequence is indicated by wavy underlining. Amino acids which are often conserved in Ig-like domains are indicated by (+). Arrow heads below the nucleotide sequence denote exon/intron boundaries identified in genomic DNA clones.

The 5' portion of mouse HB15 was isolated by PCR amplification of a mouse B lymphocyte CDNA library using a 5' oligonucleotide sense probe homologous with the flanking sequence of the vector and using a 3' antisense oligonucleotide probe (#2489 in Table 1) homologous to the 5' half of the Ig like domain of mouse HB15. This generated an approximately 400 bp cDNA fragment that was subcloned and sequenced. The nucleotide sequence of the PCR product revealed that it was nearly identical in sequence to the human HB15 cDNA (FIG. 6). RNA was isolated by a modification of the single step acid-guanidine-phenol-chloroform method from the mouse B cell line A20. One microgram of this RNA was used to synthesize cDNA using random hexamer primer oligonucleotides and SUPER-SCRIPT reverse transcriptase (Bethesda Research Laboratories). The cDNA synthesis reaction mixture contained 10 mM Tris-HCl (pH 8.3), 50 mM KCl, 1.5 mM $MgCl_2$, and 0.8 mM each of DATP, dGTP, dCTP, and dTTP (Sigma, St. Louis, Mo.), 500 ng of the hexamer primer, 200 U of reverse transcriptase, and 1 µl of RNasin (Promega) were added to give a final volume of 25 µl. After 1 hour at 37° C. this reaction mixture was stopped by heating to 95° C. for 5 min and then cooled to 4° C. for 5 min. 5 µl of this reaction mixture was used to perform polymerase chain reactions (PCR) by adding 10 µl of PCR buffer, 50 pmol sense and antisense primers and amplification was carried out for 30 cycles as follows: denature for 1 min. at 94° C., anneal for 1 min. at 55° C. and extend for 1 min. at 72° C.

The PCR amplified cDNAs were electrophoresed through 1% agarose gels and transferred to nitrocellulose. DNA size was determined by co-electropheresis of a 1-kb ladder (Bethesda Research Laboratories, Gaithersberg, Md.). Hybridization was performed at 50° C. in buffer containing a 5' end-labeled oligonucleotide, 6×NET (3M NaCl, 0.02 mM EDTA, 0.15 mM Tris-HCl ph 8.3), 10×Denhardt's solution, 0.1% SDS (w/v), 20 mM sodium phosphate, and 100 µg/ml salmon sperm DNA (Sigma). Filters were finally washed in 2×SSC at room temperature. Autoradiography was at room temperature for 30 min.

Within the immunoglobulin-like domain of human and mouse HB15, all cysteine residues have been conserved, including those which delineate the immunoglobulin-like domain in the human protein. Partial determination of intron/exon boundaries for the mouse HB15 gene has confirmed that, as with the human HB15 gene, the immunoglobulin-like domain in the mouse is encoded by at least two exons.

Mouse HB15 sequence-specific oligonucleotide primers generated from a portion of the immunoglobulin-like domain (#2406 in Table 1) and from the cytoplasmic domain (#2407 in Table 1) have been used as probes to examine the pattern of expression of HB15 in mouse. The presence of HB15-specific mRNA in spleen, kidney, liver, brain, muscle, lung, thymus, and thyroid tissue was tested by reverse transcriptase PCR and generated the expected DNA products in all organs. The identification of HB15 mRNA in multiple organ sites may reflect the presence of dendritic cell family members present as a network of supportive or accessory cells in diverse tissue types throughout the body.

Figure 8A:
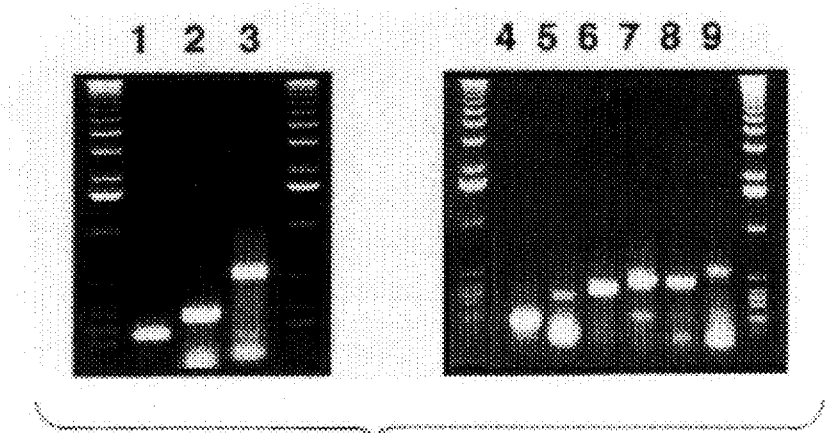
FIG. 8A shows results of PCR amplification and gel electrophoresis of amplified fragments.
Figure 8B:
FIG. 8B shows results of Southern blots of the gels shown in FIG. 8A using a probe from the HB15 transmembrane domain.

HB15 cDNAs were isolated from niRNA as follows. cDNA was produced from Raji MRNA to determine whether oligonucleotides representing different domains of the molecule (FIG. 7) could be used as probes to generate HB15 nucleotide sequences. In FIG. 7, locations of oligonucleotides used for PCR amplification of cDNA. Oligonucleotides identical to the human sequence are shown above the human cDNA while oligonucleotides identical to the mouse sequence are below the human cDNA sequence. The 5' end of the oligonucleotide is indicated by an arrowhead; > for sense primers and < for antisense primers. cDNA was amplified by PCR and the resulting products were characterized by Southern blot analysis with probes that would hybridize with internal HB15 sequence. Both the entire open reading frame and the 5' and 3' ends of cDNAs were amplified using the strategy shown in FIGS. 8A and 8B. In FIG. 8A, HB15 cDNAs were generated from RNA isolated from the Raji B cell line and the cDNAs were amplified using appropriate combinations of a sense oligonucleotide and antisense oligonucleotide, whose sequences are defined in Table 1 as follows: 1. #2083 and 2407; 2. 2406 and 2407; 3. 2085 and 2407; 4. LJZ001 and 2086; 5. LJZ001 and 2489; 6. LJZ001 and 2084; 7. LJZ001 and TFT617; 9. LJZ001 and 2407. This strategy generated cDNA fragments representing the 5' end or 3' end of the HB15 coding region. FIG. 8A shows representative results from one experiment showing the PCR amplified cDNAs obtained; PCR-generated cDNAs were electrophoresed on an agarose gel with DNA size markers and stained with ethidium bromide. In FIG. 8B, Southern blots of replicates of the gel in A were probed with the end-labeled #2082 oligonucleotide. Autoradiographic results are shown. There were additional bands variably observed in some PCR reactions, but these bands were also seen in control reactions carried out with mRNA from HB15 negative cell lines (data not shown). These bands also failed to hybridize with internal $^{32}$P-labeled oligonucleotide probe in most cases. Therefore, it is most likely that these minor species of PCR products represented artifact DNA generated in the PCR amplification process and do not represent real MRNA species.

TABLE 1

| Probe | Human/Mouse | Orientation | Domain | Sequence | SEQ ID NO: |
|---|---|---|---|---|---|
| LJZ001 | m | sense | Leader | GCC ATG TCG CAA GGC CTC CAG CTC C | 5 |
| 2086 | h | antisense | 5'Ig exon | AC ACG GTC TCC TGG GTC AAG | 6 |

TABLE 1-continued

| Probe | Human/Mouse | Orientation | Domain | Sequence | SEQ ID NO: |
|---|---|---|---|---|---|
| 2084 | h | antisense | 3'Ig exon | AC CTA AGT GGC AAG GTG ATC | 7 |
| 2085 | h | sense | 3'Ig exon | GA CAG CAC TAT CAT CAG AAG | 8 |
| 2406 | m | sense | 3'Ig exon | C TGC AGC TCG GGC ACC TAC AGG TG | 9 |
| 2489 | m | antisense | 3'Ig exon | C TGC AGC TCG GGC ACC TAC AGG TG | 10 |
| 2083 | h | sense | TM exon | T GCA CAG CGT AAA GA | 11 |
| LJ33 | h | antisense | TM exon | ACT TTT AAG AAA TAC AGA GCG GAG ATT GTC CT | 12 |
| TFT617 | h | antisense | TM exon | G AAA TAC AGA GCG GAG ATT GTC CT | 13 |
| 2082 | h | antisense | TM exon | ACA CTC ATC ATT TTC ACT TGT | 14 |
| 2407 | m | antisense | cyto.tail | A GCT TTT CTT CCA GTC ACC TCC CCA A | 15 |

EXAMPLE IV

Production of monoclonal antibodies reactive with HB15

A monoclonal antibody reactive with HB15 or an HB15 homolog or portion thereof, particularly a portion of the extracellular domain of the molecule, may be prepared as described below for preparation of the anti-HB15a and anti-HB15b antibodies.

1. Preparation of Anti-HB15a and Anti-HB15b Antibodies

Hybridomas were generated by the fusion of NS-1 myeloma cells with spleen cells obtained from mice immunized with pHB15 cDNA-transfected COS cells. COS cells were transfected with the pHB15 cDNA insert subcloned into a modified CDM8 vector (Aruffo et al., EMBO J. 6:3313 (1987); Tedder et al., J. Immunol. 143:712–717 (1989)) using the DEAE-dextran method as described (Aruffo et al., EMBO J. 6:3313 (1987)). Cell surface expression was examined after 48 hours by indirect immunofluorescence. Stable cDNA transfected cells were produced using the pHB15 cDNA cloned into the BamH I site of the retroviral vector PZIPHEESV(X) in the correct orientation (Cepko et al., Cell 37:1053–1062 (1984)). The murine pre-B cell line, 300.19, and the human erythroleukemia cell line, K562, were transfected with this vector by electroporation with subsequent selection of stable transfectants using G418 (Gibco/BRL). Cells expressing HB15 were further enriched by reacting the cells with monoclonal antibodies with the subsequent isolation of HB15+ cells by panning on anti-mouse Ig coated plates. Cell lines were grown in RPMI 1640 medium containing 10% fetal calf serum and antibiotics. Cultures of all cell lines were split the day before analysis and were in logarithmic growth.

Anti-HB15 mAb were generated as described (Tedder et al., J. Immunol. 144:532–540 (1990)) by the fusion of NS-1 myeloma cells with spleen cells from BALB/c mice that were repeatedly immunized with COS cells transfected with the HB15 cDNA. Each hybridoma was cloned twice and used to generate ascites fluid. The isotypes of the mAb were determined using a mouse monoclonal antibody isotyping kit from Amersham (Arlington Heights, Ill.).

Monoclonal antibodies reactive in indirect immunofluorescence assays with HB15 MRNA positive cell lines, but not with HB15 negative cell lines, were isolated. Two of these antibodies, anti-HB15a ($IgG_{2b}$) and anti-HB15b ($IgG_3$) also reacted with COS cells transfected with the pHB15 cDNA, but did not react with cells transfected with CD19 cDNA (Tedder et al., J. Immunol. 143:712–717 (1989)) or the expression vector alone. In addition, these antibodies reacted with a human erythroleukemia cell line, K562, and a mouse pre-B cell line, 300.19, stably transfected with the pHB15 cDNA. The antibodies did not react with untransfected parent cells, cells transfected with vector alone; or CD19, CD20 (Tedder et al., Proc. Natl. Acad. Sci., USA 85:208 (1988)) or LAM-1 (Tedder et al., J. Exp. Med. 170:123–133 (1989)) cDNA transfected cells. In all cases, the reactivities of the anti-HB15a and anti-HB15b mAb were identical.

2. Mapping of HB15 Epitopes.

A monoclonal antibody specific for a given region of HB15 may be made using a peptide corresponding to the region of the molecule as an immunogen, and using conventional hybridoma production procedures. In addition, the cross-reactivity of such antibodies can be ascertained as follows. For example, the HB15a and HB15b mAb identify different epitopes on the HB15 molecule. The HB15a mAb was conjugated to FITC (HB15a-FITC). K562 cells transfected with the HB15 cDNA were first reacted with saturating amounts of either the HB15a or the HB15b mAb in the form of diluted ascites fluid. After the appropriate incubation period, the cells were subsequently washed and then treated with HB15a-FITC. After the appropriate incubation period, the cells were washed again to remove unbound HB15a-FITC and analyzed by fluorescence-based flow cytometry. Cells pretreated with HB15a mAb did not bind HB15a-FITC since the unlabeled mAb blocked the binding of the labeled reagent. In contrast, treatment of the cells with HB15b mAb had no effect on the staining of the test cells with the HB15a-FITC. These results demonstrate that the HB15a mAb binds to a different epitope of the HB15 molecule than the HB15b mAb.

Other HB15-reactive monoclonal antibodies may be produced using the amino acid sequence disclosed in SEQ ID NO:2, and portions thereof longer than 8–10 amino acids, using antibody production techniques described herein and in the literature.

For example, monoclonal antibodies to the protein or a fragment thereof may be made by the somatic cell hybridization techniques described initially by Kohler, B. and Milstein, C., Nature (1975) 256:495–497. The procedure involves immunizing a host animal (typically a mouse because of the availability of murine myelomas) with the protein. Antibody-producing cells (e.g., peripheral blood lymphocytes, splenocytes) are taken from the immunized host and mixed with a suitable tumor fusion partner in a liquid growth medium containing a fusogen such as polyethylene glycol of molecular weight 2000 to 5000. After the fusion the cells are washed to remove residual fusion medium and incubated in a selective growth medium (i.e., a growth medium containing additives to which the parent tumor line is sensitive) such as HAT medium. Surviving hybrids may be expanded and their culture media screened for the presence of antibodies by radioimmunoassay (RIA). Positive cultures may be screened for their ability to recognize and bind to the protein by immunoprecipitating labeled cell extracts with the positive cultures and analyzing the precipitate by SDS-PAGE for the presence of a labeled component. Hybrids that produce antibody that binds specifically to the protein may be subcloned and grown in vitro or in vivo by known procedures. The antibody may be isolated from the resulting culture medium or body fluid, as the case may be, by conventional procedures for isolating immunoglobulins.

Thus, monoclonal antibodies may be made against multiple epitopes of the HB15 polypeptide or an HB15 mammalian homolog.

EXAMPLE V

Detection of HB15 expression

1. Immunoprecipitation of cell surface HB15

In order to detect the presence of HB15 or an HB15 homolog on certain cell types, an anti-HB15 monoclonal antibody may be used to immunoprecipitate the cognate antigen from a given cell type, as follows.

The anti-HB15a mAb was purified, coupled to beads and used to immunoprecipitate HB15 from detergent solubilized extracts of surface-iodinated cell lines, as follows. Cells were washed twice, resuspended in saline and labeled by the iodogen method as described (Thompson et al., Biochem. 26:743–750 (1987)). After washing, the cells were lysed in 1 ml of buffer containing 1% (v/v) TRITON X-100 and protease inhibitors as described (Tedder et al., Proc. Natl. Acad. Sci., USA 85:208 (1988)). Immunoprecipitations were carried out using anti-HB15a mAb or mouse Ig (as a negative control) directly conjugated to AFFIGEL (BioRad, Richmond, VA) at 2 mg of mAb per ml of gel according to the manufacturer's instructions. Cell lysates were precleared twice for 2 hours using 50 µl (50% v/v) of murine Ig coated beads at 4° C. Cell lysates were precleared again overnight. Half of the precleared lysate was then incubated with 25 µl of anti-HB15a mAb-coated beads or murine Ig-coated beads with constant rotation at 4° C. for 18 hours. Immunoprecipitates were washed and analyzed by SDS-PAGE as described (Tedder et al., Proc. Natl. Acad. Sci., USA 85:208 (1988)) with half of the sample run in the presence of 5% 2-mercaptethanol (reducing conditions). $M_r$ were determined using pre-stained standard molecular weight markers (Gibco/BRL).

Optimum results were obtained using the K562-HB15 cell line (K562 cells transfected with pHB15 cDNA) since the level of HB15 expression was higher than in other cell lines. The anti-HB15a mAb specifically immunoprecipitated proteins that migrated as a single broad band of ~45,000 $M_r$. Similar results were obtained when the immunoprecipitated materials were run under reducing or nonreducing conditions. A similar protein was immunoprecipitated from the Raji cell line except the $M_r$ was ~40,000. Thus, HB15 was expressed as a noncovalently-associated single chain molecule on the cell surface.

2. HB15 is expressed by activated lymphocytes

In order to determine the tissue distribution of HB15 or an HB15 homolog, an anti-HB15 monoclonal antibody may be used to identify the presence of the cognate antigen by immunofluorescence staining and/or immunohistological analysis of different tissues, as follows. Cells were kept at 4° C. and were examined immediately after isolation. Indirect immunofluorescence analysis of viable cells was carried out after washing the cells three times. The cells were then incubated for 20 min on ice with each mAb as ascites fluid diluted to the optimal concentration for immunostaining. Isotype-matched murine antibodies that were unreactive with human leukocytes were used as negative controls. After washing, the cells were treated for 20 min at 4° C. with fluorescein isothiocyanate-conjugated goat anti-mouse Ig antibodies (Southern Biotechnology Associates, Birmingham, Ala.). Single color immunofluorescence analysis was performed on an EPICS PORFILE flow cytometer (Coulter Electronics, Hialeah, Fla.). Ten thousand cells were analyzed for each sample. All tissues were stained applying a modification of the APAAP procedure as described by Cordell et al., J. Histochem. Cytochem. 31:219–229 (1984). Basically, the slides were first incubated with monoclonal antibody followed by an incubation step with rabbit anti-mouse (bridging) antibody. Subsequently, a monoclonal antibody against alkaline phosphatase pre-incubated with alkaline phosphatase was applied. In order to enhance the sensitivity of this procedure, the number of phosphatase molecules on the surface was increased by using one or two layers of bridging antibody and anti-phosphatase antibody. Bound phosphatase molecules were visualized using new fuchsin as a substrate (Cordell et al., J. Histochem. Cytochem. 31:219–229 (1984)).

Figure 4A:
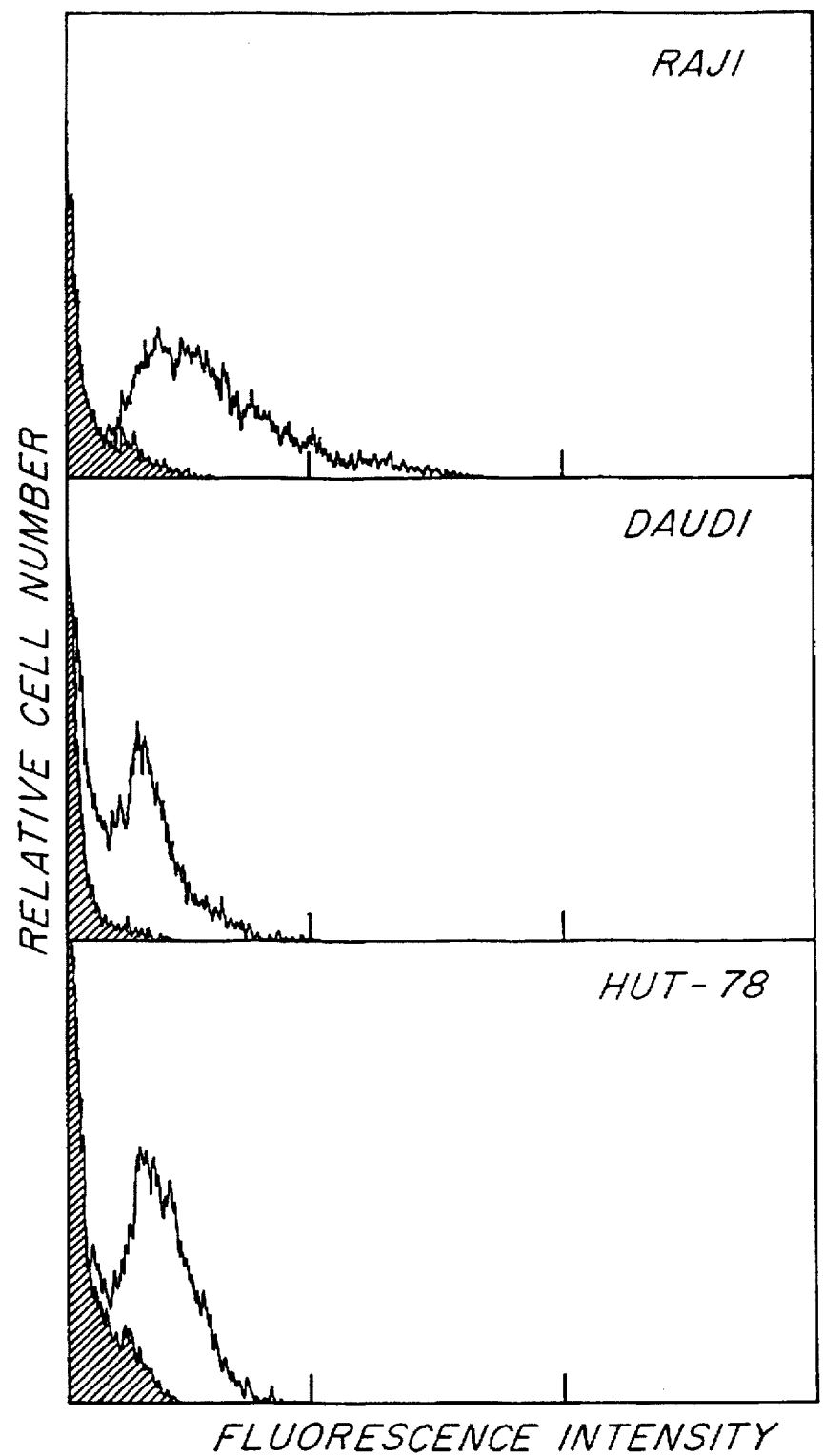
FIG. 4A shows immunofluorescence results obtained with three lymphoblastoid cell lines that express HB15 (A) with blood lymphocytes before and after mitogen activation (B); open histograms show cellular reactivity with the HB15a antibody; shaded histograms represent background levels of immunofluorescence staining obtained with unreactive control antibodies.
Figure 4B:
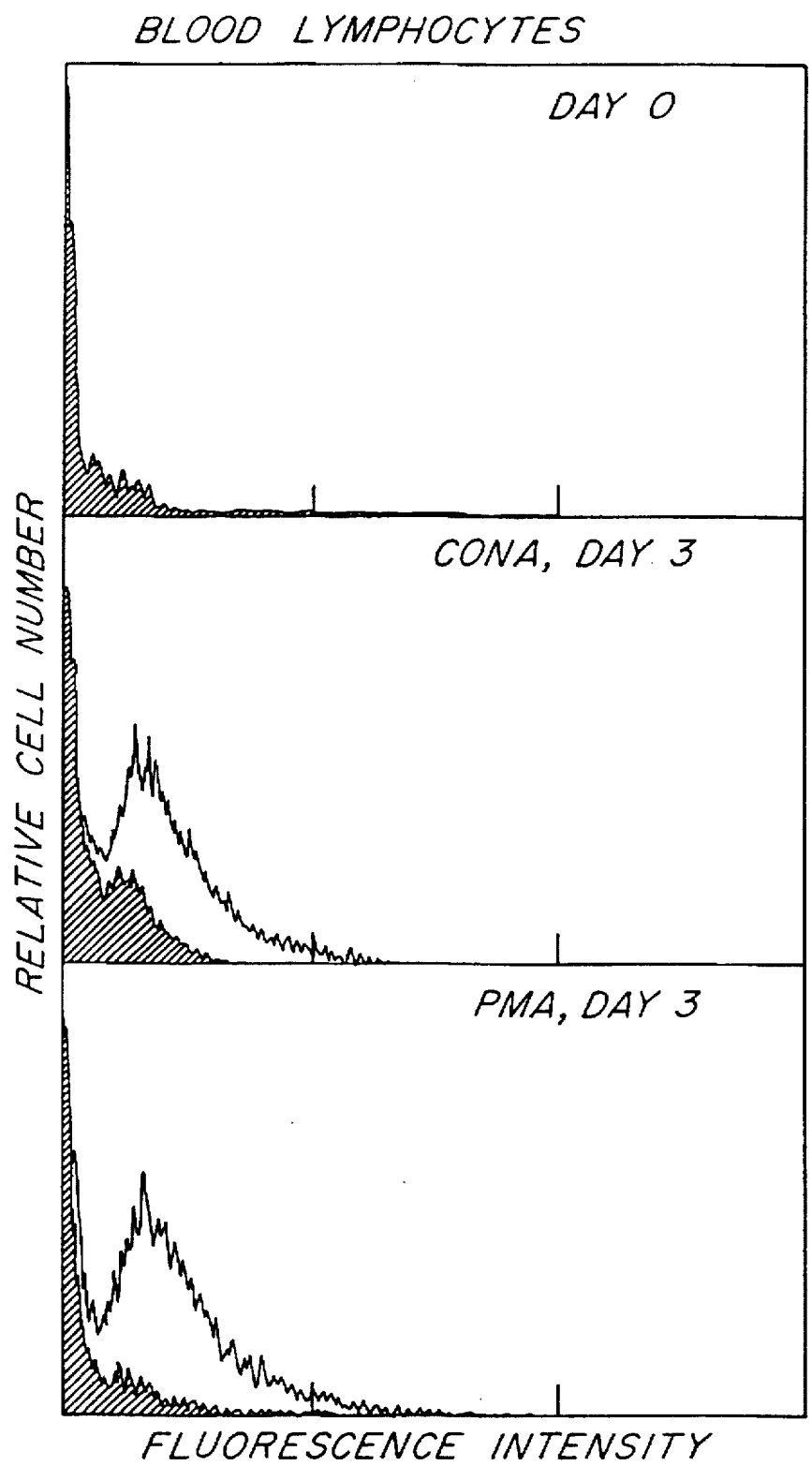
FIG. 4B shows immunofluorescence results obtained with blood lymphocytes before and after mitogen activation (B), with open and shaded histograms represented as in FIG. 4A.

The tissue distribution of the HB15 surface antigen was examined by indirect immunofluorescence staining with flow cytometry analysis. Two cell lines that did not express HB15 message were transfected with the pHB15 cDNA subcloned into the Bam HI site of the retroviral vector PZIPNEVSV(X). Referring to FIG. 4, the immunofluorescence results obtained with three lymphoblastoid cell lines that express HB15 are demonstrated. The open histograms show the cellular reactivity with the HB15a antibody, and the shaded histograms demonstrate background levels of immunofluorescence staining obtained with unreactive control antibodies. Among 33 cell lines examined, HB15 was expressed at detectable levels by B cell lines (including Raji, Daudi, Namalwa, Arent, BJAB, SB, Jijoy, Akata, and SLA) and T cell lines (including Jurkat, H-9, Rex, H-SB2, and Hut-78). However, HB15 expression was generally low and variable. The highest levels of cell-surface expression were always obtained where the cell cultures were recently split and were thus proliferating maximally. Cell lines that did not express detectable levels of HB-15 included: K562; the B cell lines NALM-6 and Ramos; the T cell lines, MOLT-3, RPMI 8405, PEER, MOLT-14, CEM and HPB-ALL; the myelomonocytic line, HL60; the natural killer cell line, YT; the colon carcinoma lines, Colo-205 and HT29; the lung cell lines, NCI-H69, and NCI-H82, the prostate line, PC3; the melanoma line, MEWO; and the breast tumor lines, ZRT5.1, MCF7 and BT20.

Expression of HB15 by normal blood leukocytes was also examined. Human blood was obtained by protocols approved by the Human Protection Committee of Dana-Farber Cancer Institute and mononuclear cells were isolated by FICOLL HYPAQUE density gradient centrifugation. Mononuclear cells ($10^6$/ml) in complete media (RPMI-1640 supplemented with 15% fetal calf serum, antibiotics and glutamine) were stimulated with phytohemagglutinin-P (2 µg/ml; Difco, Detroit, Mich.), Con A (10 µg/ml, Miles Laboratories, Elkhart, Ind.), pokeweed mitogen (10 µg/ml, Gibco/BRL, Bethesda, Md.) or phorbol myristate 13-acetate (PMA, 10 ng/ml, Sigma, St. Louis, Mo.) as described (Tedder et al., J. Immunol. 144:532–540 (1990)). Lymphocytes were harvested at the indicated time points, washed once in complete media, and aliquoted for immediate immunofluorescence staining.

Cell-surface expression of HB15 was not detected at significant levels on circulating lymphocytes, natural killer cells or monocytes in 15 blood samples. Therefore, the possibility that HB15 was expressed following cellular activation was examined by inducing T lymphocyte proliferation with the mitogens concanavalin A (ConA), pokeweed mitogen, phytohemag-glutinin-P or phorbol esters (PMA). Expression of HB15 was examined 2, 8, 12, 24, 48, 72, 120 and 240 hours following the initiation of cultures. Appearance of HB15 expression paralleled cellular proliferation such that optimal expression was on days 3 through 5 following the initiation of cultures. Also, the quantity of HB15 expression induced was not correlated with any specific mitogen, but correlated more with the strength of the mitogenic signal such that cell-surface expression was predominantly found on the larger blast cells. Therefore, HB15 was expressed by lymphocytes following activation.

3. Immunohistological analysis of HB15 expression

Figure 5A:
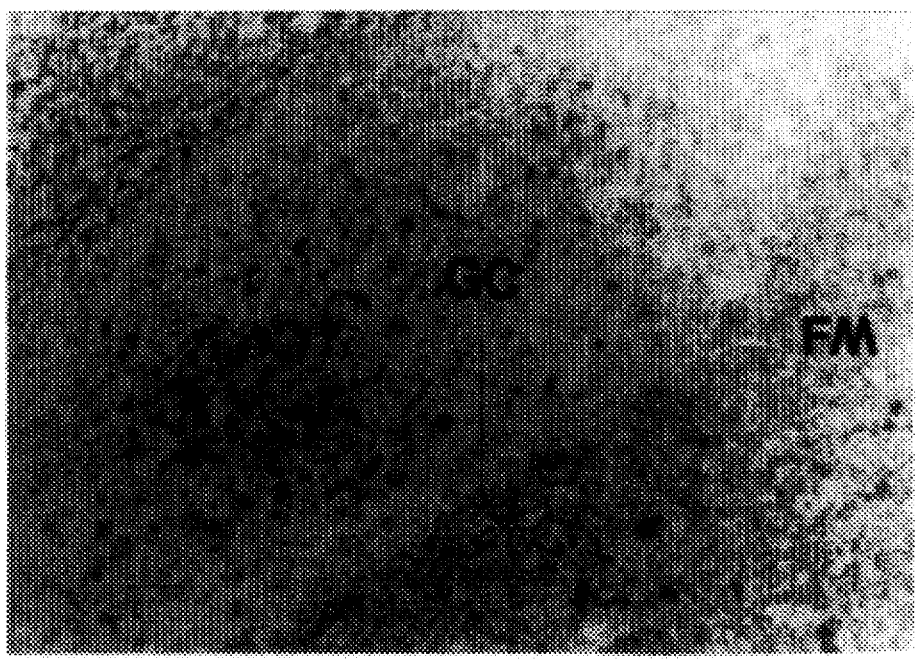
FIG. 5A shows immunohistochemical analysis of HB15 expression in tonsil and lymph node cells.
Figure 5B:
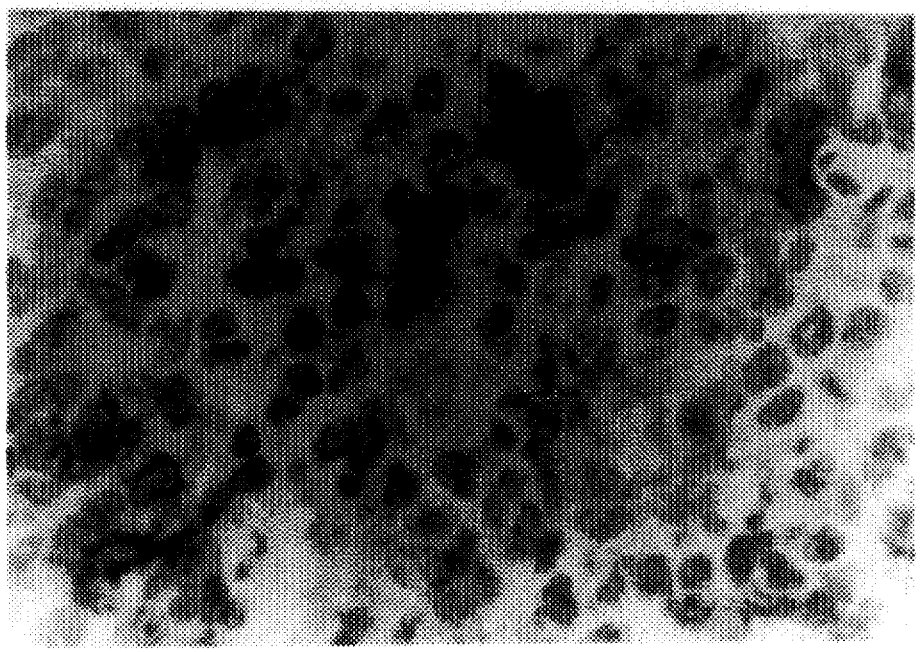
FIG. 5B shows immunohistochemical analysis of HB15 expression in germinal centers.
Figure 5C:
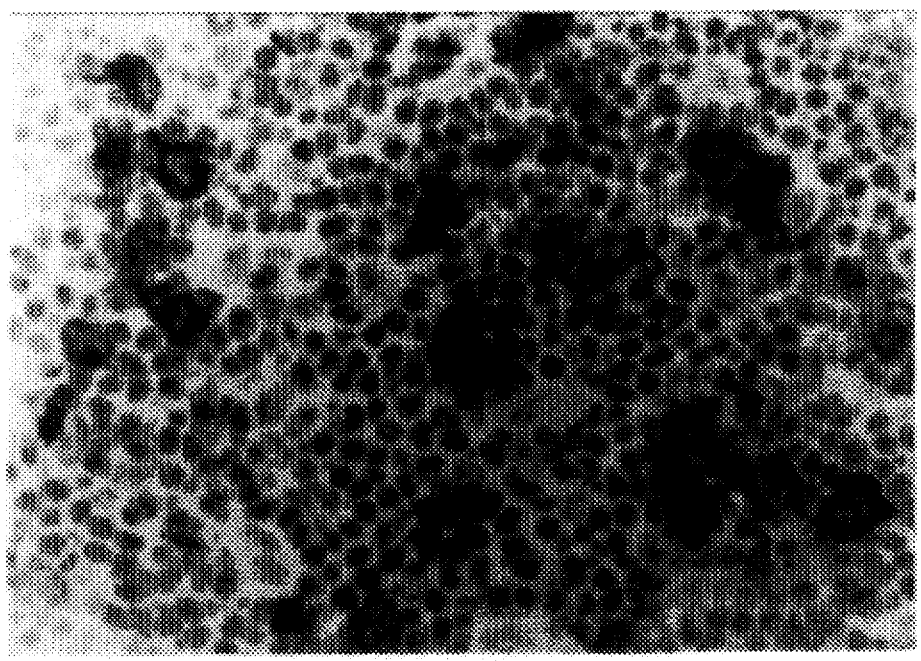
FIG. 5C shows immunohistochemical analysis of HB15 expression in interfollicular regions (i.e., the T-cell zone)
Figure 5D:
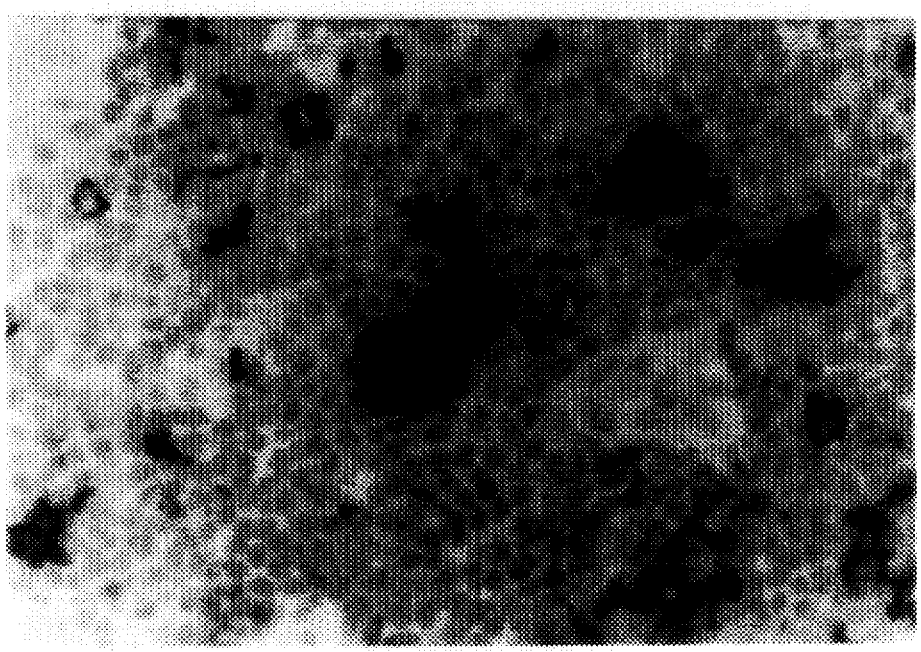
FIG. 5D shows immunohistochemical analysis of CD1 expression in a subpopulation of dendritic cells.
Figure 5E:
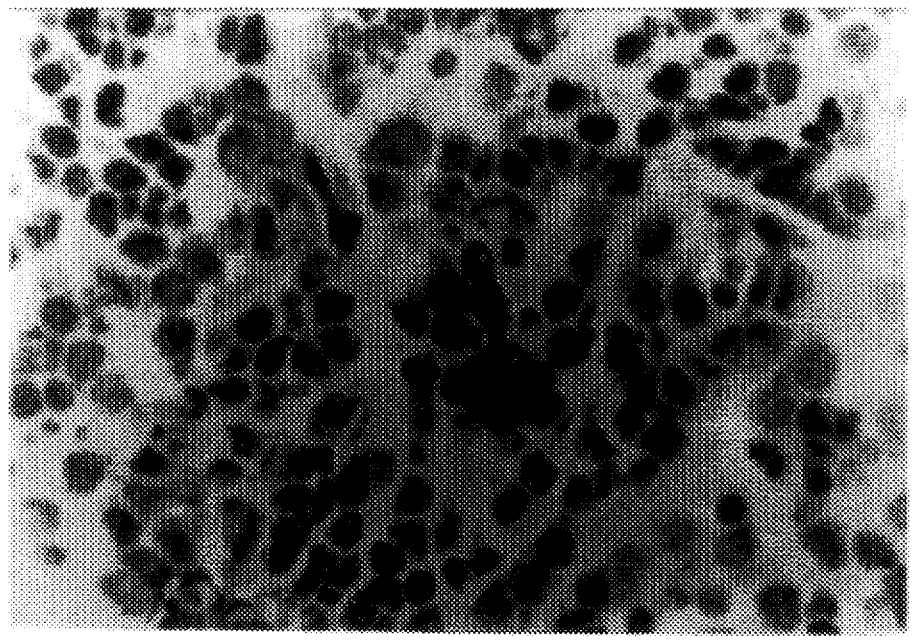
FIG. 5E shows immunohistochemical analysis of HB15 expression in a subpopulation of thymic medulla cells.
Figure 5F:
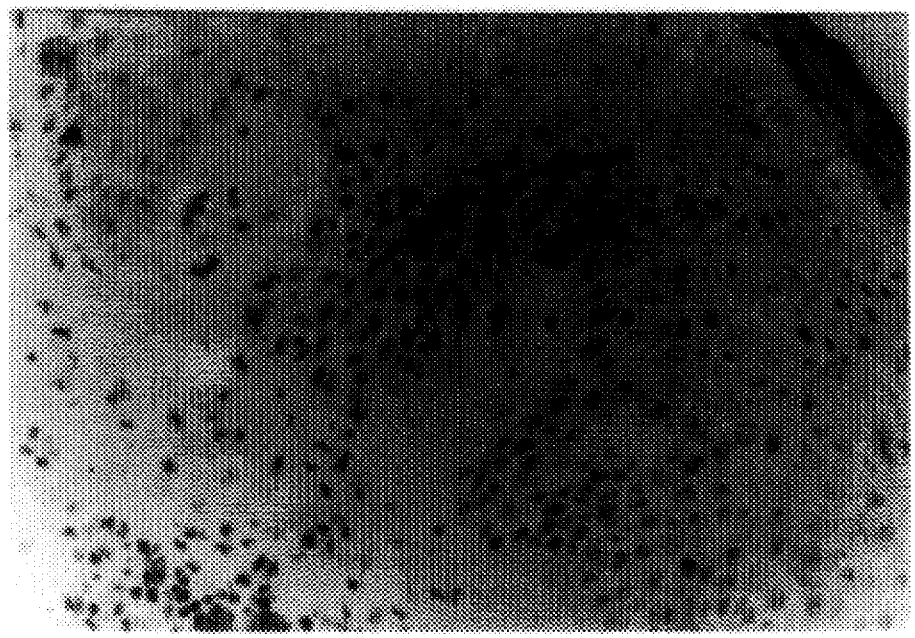
FIG. 5F shows immunohistochemical analysis of HB15 expression in a subpopulation of dendritic cells (skin Langerhan's cells).

The lymphocyte specificity and tissue distribution of HB15 was also examined by immunohistological analysis of different human tissues. Basically, the anti-HB15a mAb was used to stain thymus, tonsil, spleen, lymph node, kidney, renal pelvis and ureter, Fallopian tube, liver, pancreas, stomach, breast, lung, esophagus, skeletal muscle, skin, uterus, salivary gland, thyroid gland, adrenal gland, heart, appendix and colon. (Referring to FIGS. 5A–5F), in most cases, HB15 expression appeared lymphocyte specific in that no significant reactivity was observed in non-lymphoid tissues. Among tonsil and lymph nodes (FIG. 5A), HB15 was expressed reasonably strongly by scattered cells in intrafollicular regions (T cell zones) (FIG. 5C). Although some of these cells may have been lymphoblasts, most were interdigitating reticulum cells (a subpopulation of dendritic cells) since they appeared larger than resting lymphocytes and expressed the CD1 surface molecule (FIG. 5D). Also, some cells (50–80%) within germinal centers (GC; FIGS. 5A and 5B) and follicular mantle zones (FM; FIG. 5A), with the morphology of lymphocytes, were weakly HB15$^+$. Among spleen, the HB15$^+$ cells were predominantly restricted to the white pulp, whereas the red pulp remained largely negative. Again, these large, scattered positive cells in the white pulp are likely to be interdigitating reticulum cells or lymphoblasts. Cortical thymocytes were HB15 negative, while a small subpopulation of medullary cells, presumably thymocytes, was positive (FIG. 5E). Unlike other non-hematopoietic tissues, analysis of skin revealed that some cells with the characteristic scattered branching morphology of Langerhans cells (a subpopulation of dendritic cells) expressed HB15 at detectable levels (FIG. 5F). Among all non-hematopoietic tissues, where inflammatory infiltrations were apparent, a few scattered lymphocytes were found to express HB15. It is also likely that circulating dendritic cells are HB15$^+$, but because of their low frequency they were not readily detected. Similarly, it is also likely that the malignant counterparts of dendritic cells express HB15 and that this molecule can be used as a diagnostic marker for malignant cells as the L428 cell line, which is a neoplastic cell line that was derived from Hodgkin's disease and may represent interdigitating reticulum cells (Schaadt et al., Int. J. Cancer 26:723–731 (1980)), is HB15 positive.

It is to be understood that an HB15 homolog, like HB15 itself, will resemble HB15 in its tissue distribution pattern. That is, an HB15 homolog will be present on activated lymphocytes and generally absent on inactivated lymphocytes, although the presence or absence of the homolog on specific cell lines may not be directly correlated with the presence or absence of HB15 on such cell lines.

EXAMPLE VI

Quantitation of HB15 Levels.

Endogenous levels of HB15 polypeptide or an HB15 polypeptide homolog in serum can be quantitated using the monoclonal antibodies that have been produced against HB15 according to any one of a number of quantitation methods known to those of ordinary skill in the art, including an enzyme-linked immunoassay (ELISA). For example, a serum sample may be obtained and serially diluted prior to analysis. The dilutions may be assayed in a conventional ELISA wherein the detecting antibody is an anti-HB15 antibody described herein. Detection and quantitation of HB15 in the serum sample are performed as described in art.

Uses

The HB15 protein or immunospecific fragments thereof, or antibodies or other antagonists to HB15 function, have a variety of uses, some of which are described below.

1. HB15 as a Marker for Non-follicular Dendritic Cells.

There are at present no specific markers for non-follicular dendritic cells in humans. Use of HB15 monoclonal antibody to identify HB15$^+$ cells permits the isolation and purification of cells expressing this protein from a population of unrelated cells.

2. HB15 as a Marker for Cell Sarcomas and Malignant Phenotypes.

The HB15 monoclonal antibody will also be useful for evaluation and diagnosis of interdigitating cell sarcomas or other malignant cell types expressing this antigen. Therefore, HB15-based agents may be suitable for immunotherapy or immunoimaging. HB15 protein or immunospecific fragments thereof, or antibodies which antagonize HB15 function are useful for diagnosis or treatment of a variety of immunological disorders. For such purposes, the soluble external domain may be employed, typically but not necessarily, polymerized in a multivalent state using, e.g., dextran or polyamino acid carriers or fusion proteins of HB15 fragments and carrier molecules. Alternatively, liposomes may be employed as the therapeutic vehicle, in which case the transmembrane domain and preferably at least some of the cytoplasmic domain will also be included.

For example, since Langerhans cells are the primary immunocompetent cell in the skin, playing a role in the presentation of antigen to T cells and the induction of contact hypersensitivity, and since HB15 is expressed by Langerhans cells and may be involved in antigen presentation, it is likely to be involved in the pathogenesis of human skin disease such as psoriasis, autoimmune disorders, organ transplant and AIDS. Therefore, antagonists to HB15 function can provide important therapeutic agents for treatment of these diseases.

Similarly, since HB15 may serve as an accessory molecule for lymphocyte activation, the HB15 antigen, fragments or domains thereof, may be used as agonists that would augment or inhibit an immune response.

More specifically, the dendritic cell is a primary target of the human immunodeficiency virus, the causative agent of AIDS. It has recently been proposed that 80% of AIDS virus in vivo is produced by dendritic cells, particularly by Langerhans cells, circulating dendritic cells and interdigitating reticulum cells (Langhoff et al., Proc. Natl. Acad. Sci. USA 88:7998–8002 (1991)). Also, most infections occur through mucosal surfaces where it is thought that dendritic cells are first infected. Therefore, this reagent provides us with a critical tool for the potential prevention or treatment of AIDS or AIDS related disorders.

Certain clinical conditions may be monitored using in vitro assays to quantitate the levels of endogenous soluble HB15 in a patient's blood serum. Based on the finding that several receptors are now known to be shed during various normal and pathological conditions, it is possible that HB15 is also lost from the cell surface by an enzymatic process. Also, quantitative detection can be useful in a method of identifying leukocytes with abnormal or decreased expression of HB15 for diagnosis and/or detection of leukocyte activation or altered leukocyte function. Additionally, the ability to quantitate the amount of receptor, or fragment thereof, produced during the manufacture of a recombinant therapeutic agent will be advantageous for determining the efficacy of the agent.

Similarly, in treating certain clinical conditions, it may be advisable to remove endogenous soluble HB15 or HB15+ cells from a patient's blood. This can be done with existing on-line and off-line techniques by employing immunoselection columns containing antibodies or other binding agents directed against the disclosed external domain of HB15.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

Deposits

The following hybridomas were deposited on March 17, 1992, with the American Type Culture Collection (ATCC) under the terms of the Budapest Treaty.

| Identification | ATCC Designation |
| --- | --- |
| Anti-HB15a Hybridoma cell line, HB15a | HB 10987 |
| Anti-HB15b Hybridoma cell line, HB15b | HB 10988 |

Applicants' assignee, Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

What is claimed is:

1. An antibody that specifically recognizes a polypeptide having the sequence of the extracellular domain, the transmembrane domain, or the cytoplasmic domain of the HB15 protein having the amino acid sequence given in SEQ ID NO:2.

2. A monoclonal antibody that specifically recognizes the HB15 protein having the amino acid sequence given in SEQ ID NO:2.

3. The monoclonal antibody of claim 2, said antibody being produced by the hybridoma cell line deposited as ATCC No. HB 10987, said antibody being denominated anti-HB15a.

4. The monoclonal antibody of claim 2, said antibody being produced by the hybridoma cell line deposited as ATCC No. HB 10988, said antibody being denominated anti-HB15b.

5. The hybridoma cell line deposited as ATCC No. HB 10987.

6. The hybridoma cell line deposited as ATCC No. HB 10988.

7. An imaging agent for imaging a site of HB15 expression in a human patient comprising a monoclonal antibody that specifically recognizes the HB15 protein having the amino acid sequence given in SEQ ID NO:2, said monoclonal antibody being labeled with a detectable label suitable for immunoimaging.

8. An antibody that specifically recognizes an immunogenic polypeptide fragment having a sequence of a portion of the amino acid sequence disclosed in SEQ ID NO:2.

* * * * *